United States Patent [19]
Weiss et al.

[11] Patent Number: 4,828,543
[45] Date of Patent: May 9, 1989

[54] EXTRACORPOREAL CIRCULATION APPARATUS

[76] Inventors: Paul I. Weiss, 9646 Ravensworth, Houston, Tex. 77031; Weldon S. Guest, 2731 Essex Ter., Houston, Tex. 77027

[21] Appl. No.: 847,978
[22] Filed: Apr. 3, 1986
[51] Int. Cl.$^4$ .................... A61M 2/14; B01D 11/00
[52] U.S. Cl. .................................. 604/4; 604/6; 210/637; 210/646; 422/45
[58] Field of Search ............... 604/4, 5, 6; 210/637, 210/645–647; 417/286; 422/44, 45

[56] References Cited

U.S. PATENT DOCUMENTS

| | | | |
|---|---|---|---|
| 3,768,653 | 10/1973 | Brumfield | 422/45 |
| 3,881,483 | 5/1975 | Sausse | 128/214 R |
| 3,927,981 | 12/1975 | Vianna et al. | 422/45 |
| 4,086,924 | 5/1978 | Latham Jr. | 604/6 |
| 4,113,614 | 9/1978 | Rollo et al. | 210/637 |
| 4,231,366 | 11/1980 | Schael | 128/214 E |
| 4,350,594 | 9/1982 | Kawai et al. | 210/637 |
| 4,401,431 | 8/1983 | Arp | 604/5 |
| 4,435,170 | 3/1984 | Laszczower | 604/5 |
| 4,445,884 | 5/1984 | Kurtz et al. | 604/4 |
| 4,464,164 | 8/1984 | Troutner et al. | 604/5 |
| 4,466,804 | 8/1984 | Hino | 604/4 |
| 4,490,134 | 12/1984 | Troutner | 604/5 |
| 4,493,693 | 1/1985 | Bilstad et al. | 604/6 |
| 4,514,295 | 4/1985 | Mathieu et al. | 210/90 |
| 4,596,549 | 6/1986 | Minami | 604/5 |
| 4,606,826 | 8/1986 | Sand et al. | 210/646 |

FOREIGN PATENT DOCUMENTS

| | | |
|---|---|---|
| 3043682 | 10/1980 | Fed. Rep. of Germany . |
| 3122756 | 9/1981 | Fed. Rep. of Germany . |
| 2063677 | 9/1971 | France . |
| 0085016 | 3/1983 | France . |
| 8002376 | 11/1980 | PCT Int'l Appl. ............ 604/4 |

OTHER PUBLICATIONS

"Bentley ATS-P Autotransfusion Unit: Operator Error or Design Deficiency?", *Health Devices Sourcebook*, Dec. 1982, pp. 50–51.
Twiss: "The History of Single-Needle Dialysis," *First International Symposium on Single-Needle Dialysis*, ISAO Press, Cleveland, 1984.
Leonard: "Flow Patterns of Single-Needle Dialysis," *First International Symposium on Single-Needle Dialysis*, ISAO Press, Cleveland, 1984.
Hoenich, et al.: "Review of Mechanical Systems for Single-Needle Hemodialysis," *First International Symposium on Single-Needle Dialysis*, ISAO Press, Cleveland, 1984.
Troutner: "Evolution of Single-Needle System Dialysis," *First International Symposium on Single-Needle Dialysis*, ISAO Press, Cleveland, 1984.

*Primary Examiner*—Stephen C. Pellegrino
*Assistant Examiner*—Ralph Lewis
*Attorney, Agent, or Firm*—David A. Rose

[57] ABSTRACT

A method and apparatus for extracorporeal circulation and treatment of blood. The apparatus comprises means for circulating and for treating blood, with a control system for controlling the circulating means. The circulating means includes tubing that directs blood to and from a microporous membrane. An arterial pump controls the flow rate of blood entering the filter; a venous pump controls the flow rate of blood exiting the filter. The filter includes a sealed, ported chamber surrounding the membrane. The rate of filtration of components removed from the blood through the membrane is directly proportional to a transmembrane pressure.

Display and input devices transmit information between the central processor and an operator who operates the apparatus. The display and input devices include a keypad and an alphanumeric display. Sensors measure pressures within the tubing, at the inlet and outlet of the filter. Fluid flow rate can be calculated from the speeds of the pumps.

The control system includes a central processor that receives input data from the sensors and the pumps to regulate the apparatus. The central processor will regulate the venous pump to maintain a specified outflow rate. The central processor also will maintain a desired average transmembrane pressure while the venous pump rate remains constant. The central processor calculates the average transmembrane pressure based on the measured filter input and output pressures. The central processor regulates the arterial pump speed as necessary to achieve the desired transmembrane pressure, while the venous pump rate is held steady.

54 Claims, 5 Drawing Sheets

EXTRACORPOREAL CIRCULATION APPARATUS

BACKGROUND OF THE INVENTION

The present invention relates generally to the field of extracorporeal circulation of bodily fluids. More particularly, it relates to circulation and processing of blood outside the body. Still more particularly, it relates to regulating the rates and pressures of blood flowing through an extracorporeal processing circuit.

The human body is a complicated organism. It carries out a myriad of functions and processes around the clock, day-in and day-out. Sometimes the body is unable to perform vital tasks completely or adequately. Circumstances sometimes require medical treatment to assist or replace bodily functions. Medical science has devised various machines and equipment to help the systems of the body meet the demands placed on them in ordinary and extraordinary situations. One system extremely crucial to proper operation of the body is the cardiovascular system.

The cardiovascular system includes the heart and all the blood vessels in the body. The heart provides force to pump blood through the system. The arterial system connects to the heart and fans out in increasingly smaller vessels to the far reaches of the body, linking ultimately to capillaries. Capillaries are the smallest vessels in the cardiovascular system. Capillaries form minute networks throughout the body's tissues. The capillaries eventually connect to veins. Veins, constituting the venous system, lead finally back to the heart.

Blood is a highly complex fluid. It contains, generally, plasma and cells. The cell component comprises red blood cells, white cells, and platelets. Plasma is mostly water with a tremendous variety of solutes. These solutes include inorganic components, metaboli nutrients and byproducts, and a host of plasma proteins.

Blood flows from the heart to the arteries, then to the capillary network. The blood brings nutrients and oxygen to the cells of the body. All cells need these substances to live. The blood also gathers carbon dioxide and other waste products resulting from the body's metabolism. These wastes must be removed to allow cells to continue functioning. The returning blood collects in the veins and flows back to the heart. This returning blood carries the collected waste. The kidneys treat the blood to remove such waste products. These wastes, if left in the blood, would ultimately be fatal. Kidneys perform the vital function of cleansing the blood. Lungs likewise help to rejuvenate the blood. The major function of the blood's red cells is to transport oxygen from the lungs to body tissues and to help transport carbon dioxide from the tissues back to the lungs. The heart pumps returning venous blood to the lungs. The lungs contain semipermeable membrane tissue that allows gases to migrate across it. Carbon dioxide passes from the blood into the lungs to be exhaled, while oxygen in the lungs is absorbed by the red blood cells. This newly oxygenated blood then returns to the heart for subsequent re-circulation through the cardiovascular system.

The process of circulating, cleansing, and oxygenating ;the blood, then, is essential to life. The natural mechanical and biochemical systems of the body, when operating properly, perform these tasks best. Sometimes, though, a medical patient's condition prevents proper functioning of the blood system. The ability to supplement or replace the blood system then becomes crucial to the patient's survival.

Existing extracorporeal circulation apparatus for treating blood generally remove and collect a patient's whole blood, circulate the blood through an extracorporeal circuit, and return the treated blood to the patient. Depending on the specific application, the treating involves filtering, removing some component(s) from the blood, or oxygenation. Various techniques and apparatus have been used in different blood treatment applications.

One type prior art apparatus for filtering blood includes one or more pumps and a filter combined to accomplish the extracorporeal treatment. The pump and filter are connected in series to make up the extracorporeal circuit. The pump is typically a peristaltic, or roller, pump equipped with flexible flow tubing. The pump rollers push the blood through the tubing, pressing against the tubing as the rollers spin. The pump naturally pressurizes the blood while pushing it through the tubing. Such roller pumps may have springs holding the rollers in place, or the pump construction may allow the distance of the rollers from the pump rotor center to be adjustable. Depending on the application and the type of pump, the rollers may be adjusted to occlude the tubing fully, or to squeeze it only partly, as they spin. Some operators or applications favor partially occluded tubing, since fully occluded tubing is more likely to cause hemolysis, i.e., shearing of red blood cells, where the rollers impinge on the tubing and squeeze the blood.

The filter in many applications is a microporous membrane filter. A microporous membrane filter includes a sealed, ported exterior chamber surrounding microporous membrane material. The membrane encloses an interior space for the flow of blood therethrough. The membrane may be in the form of flat plates, coils, or hollow fibers. The exterior chamber is a sealed chamber equipped with one or more ports. Using hollow fibers, for example, blood flows from the pump, through the circuit, and into the interior passageways inside the hollow fibers. The pressure of the blood flowing through the fibers derives from the pressure of the blood leaving the pump. Friction constantly reduces the pressure as the blood flows downstream from the pump and through the fibers and, therefore, the pressure inside the fibers is never more than the output pressure at the pump.

If the pressure inside the fiber exceeds the pressure in the surrounding exterior chamber, this pressure differential (called "transmembrane pressure") tends to force the blood through the membrane wall of the fiber. This fiber membrane wall contains extremely small-diameter pores. These pores are too small for the larger blood components to pass through. Thus, the red blood cells, white cells, and platelets continue flowing through the interior of the fiber. Water and other components—those small enough to pass—are pushed in varying quantities through the membrane pores. The smaller the components, the easier they will flow through the fiber membrane and into the exterior chamber, for a given pore diameter. Similarly, a greater transmembrane pressure causes a higher rate of filtration, i.e., a higher rate of flow of filtered components into the exterior chamber. The more the fiber interior pressure exceeds the exterior chamber pressure, the greater the force exerted to push components through the membrane and into the chamber.

The single upstream pump and a filter, with the exterior chamber of the filter at atmospheric pressure, are adequate for some applications. Removal of plasma ("plasmapheresis") can be accomplished with such an apparatus. Blood flows from a patient, to the pump, to the filter, and then through the hollow fibers. The exterior chamber stays at or above atmospheric pressure. The net transmembrane pressure is enough, given the type of fibers commonly used, to remove plasma from whole blood before returning blood to the patient. This simple, single pump and filter apparatus is inadequate, however, for some applications involving flow to and from a patient due to an imposed ceiling on transmembrane pressure. Speeding up the pump will raise the fiber interior pressure and, hence, the transmembrane pressure. Higher transmembrane pressure causes faster filtration. Running the pump faster, though, also increases the system inlet and outlet flow rates. A higher flow rate thereby forces a patient to deliver and receive blood faster if there are no inlet and outlet accumulation devices to act as buffers for temporary storage of blood. The patient's cardiovascular system, however, cannot circulate blood faster than some maximum allowable rate, and thus imposes a limit on the possible blood flow rate. This limitation is especially a potential problem with patients suffering from weakened hearts, restricted blood vessels, and the like. More significantly, the nature of the blood itself limits the possible rate allowable wiht just an inlet pump, even if accumulation devices are available. An excessively high flow rate (typically, above approximately 400 cc. of blood per minute) creates high shear stresses that cause hemolysis. The intent is to treat blood, not to destroy good cells. Hence, the flow rate is severely restricted even when using blood accumulators. The transmembrane pressure ceiling created by the flow rate limitation is a significant handicap when faster removal of undesirable components is needed and/or higher transmembrane permeability (resistance to filtrate flow) exists. The patient's circulatory system and the nature of blood cells, then, ultimately limit the transmembrane pressure attainable with a simple pump and filter apparatus. The pump cannot pump blood faster than it can be collected from or returned to the patient's cardiovascular system, nor faster than the blood can be filtered without destroying red cells.

Instead of merely pumping the single inlet filter faster, a higher transmembrane pressure can be created by partially occluding the tubing downstream of the filter. Partially occluding the tubing in this manner will obstruct flow therethrough, imposing a "back pressure" on the system. This back pressure will result in an elevated pressure at the filter outlet, causing a higher transmembrane pressure. The relationship between average transmembrane pressure and the pressures at the filter inlet and the filter outlet may be expressed as follows (assuming the exterior chamber gage pressure is zero, i.e., atmospheric):

$$TMP = P_o + [\tfrac{1}{2} \times (P_i - P_o)]$$

where:
TMP = Average Transmembrane Pressure
$P_i$ = Filter Inlet Pressure
$P_o$ = Filter Outlet Pressure It can be seen, then, that back pressure arising from partial occlusion downstream will raise the average transmembrane pressure in the filter by raising the filter outlet pressure even while the flow rate and filter inlet pressure remain unchanged.

Such partial downstream occlusion, however, is not a complete solution to the system's limitations, and in fact creates new problems. First, partial occlusion itself will hemolyze blood cells. The blood pressure drops suddenly and precipitously as the blood squirts through the partial occlusion. The resulting shear stress hemolyzes blood cells at a high rate. In contrast to the hemolysis occurring at a pump roller, in which only those cells at the point of roller contact with the tubing are affected, a much greater percentage of cells passing through a partially occluding device will experience high shear stress. Secondly, the transmembrane pressure in the filter is subject to variations and fluctuations due to similar changes occurring external to the filter. Pressure upstream of the point of partial occlusion will reflect the pressure downstream. The pressure downstream of the partial occlusion point will vary in accordance with numerous factors, depending on the system configuration. If the blood returns directly to a patient, for example, the patient's cardiovascular pressure will affect the transmembrane pressure in the filter. Similarly, if blood exits the filter to enter into the base of an accumulation device, the hydrostatic pressure imposed by the accumulating blood will affect the transmembrane pressure. Merely partially occluding the filter outlet to raise transmembrane pressure, then, will not cure the defects in a single pump and filter apparatus.

There is, moreover, lack of precision and certainty in predicting and controlling the rate of the filtering process through the membrane. The transmembrane pressure fluctuates with the pressure at the pump outlet. In addition, the filter permeability may vary as fibers and pores become clogged with blood elements. Lastly, if the pump rollers do not fully occlude the tubing, the pump outlet pressure may be slightly affected by the pressure at the pump inlet. Some prior art methods have been devised to observe the filtration rate, and to adjust the system in response to the observed results. For example, the removed components can be collected and their volume measured. Or the patient undergoing treatment can be continually weighed and the volume of filtered components determined from the weight measurements. Knowing the rate of filtration, in either case, requires periodically determining the cumulative volume removed and calculating the rate of removal over time. Typically, an operator notes the results of the filtration to determine this removal rate. If the filtration rate is slower or faster than that desired, the operator will adjust the pump speed to achieve the desired rate. The prior art thus provides only indirect, irregular, and imprecise means for monitoring and adjusting the apparatus to achieve desired filtration rates. The end result is unpredicatability of the rate of filtration and a need for a technician's continual attention and assistance during the operation of the machine.

Heart-lung machines used during surgery pump and oxygenate blood, in place of a patient's heart and lungs. Existing oxygenators suffer from imprecise control and inefficient operation. Blood flows through semi-permeable hollow fibers or channels inside semi-permeable membranes. Utilizing at least one pump in series with the oxygenator, the blood is pressured sufficiently to flow in the form of thin film layers along the membrane walls, thereby maximizing the flowing surface area. The partial pressure of oxygen on the exterior of the membrane walls is kept sufficiently high for the red cells of the venous blood to absorb the oxygen; similarly, the partial pressure of carbon dioxide on the membrane exterior is low enough to allow the venous red cells to discharge carbon dioxide. Oxygen on the membrane exterior migrates across the membrane for absorption by the blood, and carbon dioxide exits the blood and migrates to the membrane exterior. Inadequate control of the transmembrane pressure, however, often requires recirculation of the blood through the circuit after initial oxygenation. What pressure control exists is merely regulation of pump speeds as an indirect, and inaccurate, means for maintaining hoped-for pressure differentials. There is no true, direct control of oxygenation based on transmembrane pressure. Instead, direct observation of blood colors and pressures ordinarily helps ascertain if blood leaving the system has been properly oxygenated. Such crude operational methods demonstrate the need for improved, effective, efficient control of blood oxygenating apparatus.

A partial solution to some of the operational limitations imposed by a simple pump and filter apparatus has been the application of a vacuum (relative to atmospheric pressure) in the filter's exterior chamber. As defined previously, the transmembrane pressure is the difference between the higher fiber interior pressure and the lower exterior chamber pressure. Since the need to prevent hemolysis of red cells and, sometimes, the patient's maximum allowable blood flow rate, together impose a ceiling on the interior pressure, an apparatus placing a vacuum in the exterior chamber permits a greater transmembrane pressure than obtainable otherwise.

Vacuum-assisted filtration apparatus have found favor in some applications. One especially useful application has been in apparatus for retransfusion of a patient's own blood, termed "autotransfusion," during surgery. For various reasons, the patient's blood requires filtering before it can be returned to the patient. Accumulate blood collected from the surgical area must be cleansed of clots and other contaminants before returning to the patient. Further, some operations, such as open-heart surgery, require heart-lung machines to replace the functioning of the patient's heart and lungs during the course of the operation. The machine must be primed with fluid before it can pump any blood out of the patient. Without priming, the machine would pump air into the patient's cardiovascular system, creating an embolism and leading to almost certain death. Priming can require up to two liters of fluid. Priming with packaged "units" of blood from a blood bank is an expensive and wasteful proposition, even if this quantity of blood is available. Saline or glucose solutions are ready, inexpensive, and often utilized, but they dilute the patient's blood. At the conclusion of surgery, the blood then needs reconcentration.

With vacuum-assisted filtration, the excess volume of non-cellular fluid, i.e., other than blood cells and platelets, can be removed readily and relatively quickly from the blood stream, thereby reconcentrating the blood. A preferred method, moreover, for lowering a patient's blood pressure during surgery is to reduce the quantity of fluid in the patient's cardiovascular system. To reduce the total volume of fluid, it is preferable to filter and remove undesirable components, such as saline, rather than whole blood. The transmembrane pressure attainable with vacuum-assisted filtration enables treatment and removal of more fluid and contaminants than feasible or practical with a single pump flowing blood into a filter.

Another frequent application for vacuum-assisted filtration is conventional hemodialysis, or simply dialysis, using two needles. Dialysis is the filtering of metabolic waste products from the blood of patients suffering from renal, or kidney, failure. Such waste products are toxic and, if not removed, can be fatal to the patient.

In conventional two-needle dialysis, the patient's blood flows through a needle and into the dialysis circuit. A roller pump forces the blood through a dialyzer, typically a hollow fiber filter. Blood then flows through the return circuit back to the patient via a second needle. The exterior chamber of the filter has two ports—an inlet and an outlet. To attain the needed transmembrane pressure, dialysate fluid is pumped at a vacuum through the exterior chamber and around the exterior of the hollow fibers. Since some dialysis patients experience negative side effects from the dialysate fluid, sometimes only a vacuum, without dialysate, is applied to the exterior chamber, as in the vacuum-assisted filtration apparatus previously described with respect to autotransfusion.

While the vacuum-assisted filtration apparatus achieves greater transmembrane pressure, the vacuum-assisted apparatus still presents significant problems. First and foremost, control of the vacuum is troublesome and inaccurate. The level of vacuum is not easily regulated. This leads to uneven transmembrane pressures and more complex control equipment. With greater complexity, reliability is lessened. Secondly, the problem of lack of predictability and precise control over the rate of filtration of undesirable components is compounded. Since a vacuum pump continually pumps from the exterior chamber, any filtered components are immediately withdrawn. Such filtered components are then lost, or at least difficult to gather and monitor with conventional vacuum pumps. Finally, vacuum pumps require extensive maintenance, thus reducing their reliability. A roller pump needs less maintenance, and is more dependable. A roller pump, however, can supply vacuum only when used to draw dialysate fluid through the exterior chamber. When dialysate is undesirable, then, the more inaccurate, unreliable vacuum pump is necessary. So, the vacuum-assisted method is by no means a panacea for the problems of transmembrane filtration.

A third type prior art apparatus uses an alternating flow of blood into and out of the circuit. This apparatus has an upstream (arterial) pump, a filter, and a device for occluding the flow downstream of the filter while the arterial pump runs. This method allows the fiber interior pressure to increase to the pressure limits of the pump, unaffected by inflow or outflow limitations. Blood is accumulated in a compliant storage sac as the pump continues to run. A single pressure sensor measures the trapped blood pressure. When the fiber interior pressure reaches some predetermined level, the arterial pump stops and the occluding device opens. The contained pressure then propels the blood back to the patient, or alternatively, a second, venous pump (downstream of the filter and any storage sac) pumps the blood back, to quicken its return. When the blood pressure drops to a set lower limit, the venous pump (if there is one) stops, and the occluding device again closes. The arterial pump begins pumping again, for another cycle. The lower pressure limit ensures the blood pressure will stay at least a minimum level above ambient atmospheric pressure. The end result is a pulsatile blood pressure, varying between upper and lower limits.

This alternating-flow method is used in single-needle dialysis. Single-needle dialysis is an alternative to the conventional double-needle technique. In a single-needle dialysis apparatus, blood flows to and from the patient through one needle, with flow alternating in direction through that needle. This single needle thus requires only one puncture in the patient, instead of two. This single puncture has been a prime motivation for using the single-needed technique. The preferred method has the arterial and venous roller pumps working in tandem to create the pulsatile positive pressure within the hollow fibers. The pump rollers are set to occlude the tubing fully so the pumps block the flow when they are stopped. The exterior chamber remains at atmospheric pressure.

Using this alternating-flow method, the fluctuating positive fluid pressure in the fibers causes transmembrane pressure to oscillate over time. Less filtration occurs with lower transmembrane pressure. In contrast with a vacuum-assisted filter having a comparable, steady transmembrane pressure, the fluctuating transmembrane pressure takes longer to filter the same fluid. Some blood is filtered at a high transmembrane pressure, while other blood is filtered at progressively lower transmembrane pressures. This pressure variation thus reduces the efficiency of filtration. The average transmembrane pressure is between the upper and lower limits. Raising the peak pressure raises the average pressure, but at a cost of increased strain on equipment and possible loss through filtration of desired elements. Thus, the alternating-flow method has disadvantages.

Another hazard arises when alternating the flow through the filter, while the arterial roller pump is off and occluding the tubing upstream of the filter, and the venous pump is pumping blood from the filter. If allowed to run too long, the venous pump will create a vacuum inside the filter, drawing fluid from the exterior chamber into the blood inside the filter. Whether the fluid is air, dialysate, or anything else, the end result is to contaminate the blood, endangering the patient. To prevent this danger, prior art apparatus employing the alternating-flow method have included a pressure monitoring device to alert the operator if a vacuum were to occur within the filter. A pressure monitor, however, is prone to failure. Such failure can be deadly when a single monitor provides the only level of safety preventing contamination of the patient's blood.

Given the inefficiency of filtration and the limited level of safety against the hazard of blood contamination, the alternating-flow techinque has clear disadvantages.

Another problem common to all the various types of prior art apparatus involves the need to prime the system before initial use. A common safety device included in the circuit is a bubble detector that monitors blood flowing through the tubing for presence of air or other gases that could harm the patient. The circuit typically includes means for manually disarming the bubble detector, allowing operation of the apparatus with the bubble detector disengaged or bypassed. Before initial pumping to the patient, the tubing is empty and must be primed with a suitable fluid to prevent injection of air. The operator disarms, or bypasses, the bubble detector while the tubing is empty, primes the circuit, then should re-arm the bubble detector before beginning treatment. Not infrequently, due to human error or carelessness, the bubble detector remains in the bypass mode. Gas can enter the blood, flow undetected through the system, and be injected into the patient. The result can be lethal. Considering the limited level of safety preventing blood contamination in a single-needle, alternating-flow dialysis machine, for example, prior art apparatus can pose grave risks to a patient's health and life.

A fourth solution to the problem of achieving and maintaining adequate transmembrane pressure has been to device special filters that operate effectively with lower transmembrane pressure. Such filters do not use pumps, but remove undesirable products from blood unassisted by anything other than the pressure from the patient's own cardiovascular system. The patient's arterial blood flows directly to the filter, through it, then back to the patient's venous system. These highly permeable yet selective filters, however, are very expensive compared to the relatively simple, inexpensive, widely used hollow-fiber, microporous membrane filters. These special filters also, like the previously discussed methods, fail to provide precise control of the filtrate flow.

It is apparent that extracorporeal circulation and treatment of blood is a necessary, vital process for a wide range of medical treatments. Known apparatus for performing this process have suffered from numerous inefficiencies, operational problems, inadequate regulation, and economic disadvantages. A serious need has existed for an efficient, simple, controllable, yet economical means for circulating and treating blood outside the human body.

SUMMARY OF THE INVENTION

Accordingly, there is provided herein a new and improved method and apparatus for the extracorporeal circulation and treatment of blood. The extracorporeal circulation apparatus of the present invention comprises means for circulating and means for treating blood, with a control system for controlling the circulating means so as to determine the results and output of the blood treatment.

The circulating means includes means for establishing and regulating fluid flow to and from the treatment means. The circulating means generally includes a conduit, such as flexible plastic tubing, for containing and directing the fluid flow. The circulating means further includes means for regulating the rate or pressure of fluid flow both upstream and downstream of the treatment means. The regulating means may further include an upstream, or arterial, pump for control of the rate or pressure of fluid entering the treatment means. The regulating means may also further comprise a downstream, or venous, pump for governing the rate or pressure of fluid exiting the treatment means. The arterial pump and the venous pump operate independently to achieve desired flow or pressure conditions within the treating means.

The treatment means provides for effecting changes in the flowing fluid as dictated by the medical treatment needs. The fluid being treated flows through the treatment means. The treatment means may include a filter for removing unwanted components. The filter may include, for example, flat plates, coils, or hollow fibers constructed of microporous membranes. The membrane wall allows particles of sufficiently small size to pass through pores in the membrane. The filter further includes a sealed, ported chamber exterior to the membranes. Filtered components flow across the membrane, into the chamber, and out a port. Differential in pressure between the membrane interior and the membrane exterior is termed transmembrane pressure. The rate of filtration of components across the membrane is directly proportional to the transmembrane pressure.

The treatment means may alternatively include any fluid treatment means with operating characteristics affected by pressure and flow rate of the treated fluid. The treatment means accordingly may include an oxygenator or other device for expulsion or absorption of components by the treated fluid.

The control system may include a central processor having both communication hardware and operational hardware. The communicaton hardware transmits information between the central processor and a technician, or operator, operating the apparatus. The communication hardware may include display equipment and an input device. The display equipment includes an electronic alphanumeric display that can both prompt the operator for input and display relevant operating parameters. The input device is a keypad by which the operator enters chosen values for variables that govern operation of the apparatus.

The operational hardware may include both monitoring devices and control devices. Monitoring devices may include sensors to measure pressures and/or flow rates of the fluid within the circulation means or the treatment means. The sensors include pressure sensors that measure fluid pressure substantially at the inlet and/or the outlet of the treatment means, as necessary. The sensors also include means to measure the flow rate of fluid upstream and/or downstream of the treatment means. Fluid flow rate can be measured directly, or by monitoring of the speeds of the arterial pump and/or the venous pump, thereby to provide for calculating fluid flow rates through the monitored pump.

The control devices may include means for regulating the flow into and out of the treatment means. Motor controllers provide direct speed regulation of the arterial pump and the venous pump.

The central processor receives input data and regulates the appropriate elements of the apparatus to achieve the desired results entered into the keypad. The operator inputs a desired outflow rate from the apparatus, and the central processor regulates the venous pump motor controller accordingly. The operator can vary the outflow rate at any time by entering a new outflow parameter into the keypad. The central processor will regulate the venous pump motor controller to achieve the newly specified outflow rate. The operator may also enter a desired average transmembrane pressure to be maintained within the treatment means while the venous pump provides the specified output rate. The central processor calculates the average transmembrane pressure based on the measured input and output pressures of the treatment means. To adjust the calculated transmembrane pressure, the central processor signals the arterial motor controller to regulate the arterial pump speed as necessary while, again, the venous pump produces the specified outflow rate.

Alternatively, the operator can select a preferred rate of filtraton across a membrane of the filter, along with the specified outflow rate. The central processor compares the calculated flow rates through the arterial pump and the venous pump. The difference between the arterial and venous flow rates is the net filtration rate. With the venous pump rate held constant, the central processor adjusts the arterial pump speed as needed to maintain the desired filtration rate.

The present invention provides for the first time an apparatus and method for directly, precisely, and continually controlling either transmembrane pressures or membrane filtration. Two pressure sensors, one on either side of a filter, provide a simple yet complete means for monitoring the crucial pressures at the filter. Two pumps, one also on either side of the filter, provide separate means for controlling the output flow rate and the flow and pressures at the filter, independently of conditions elsewhere in the extracorporeal circuit. A control system enables precise, predictable, dependable regulation of the apparatus with continual feedback from and adjustment of the apparatus. An apparatus embodying the invention provides all these advantages while being capable of use with standard, inexpensive, readily available filtering devices. Application of the principles of the invention can improve equipment reliability, lower costs, avoid waste of valuable substances, and reduce risks of disease.

These and various other objects and advantages of the present inventon will become readily apparent to those skilled in the art upon reading the following detailed description and claims and by referring to the accompanying drawings.

BRIEF DESCRIPTION OF THE DRAWINGS

For a detailed description of the preferred embodiment of the invention, reference will be made to the accompanying drawings wherein.

DESCRIPTION OF THE PREFERRED EMBODIMENT

Extracorporeal circulation of blood generally involves removal and return of a patient's blood, with some appropriate treatment of that blood. Typically, treatment includes flowing the whole blood through some filtering means to remove undesirable components from the blood. One common type of filter has a microporous or semipermeable membrane that selectively filters these undesirable components. The blood flows under pressure through an interior space enclosed by the membrane. The exterior space surrounding the membrane is at a different pressure, usually lower than the interior pressure. The differential between these pressures is termed the transmembrane pressure. The rate of flow of undesirable components across the membrane is dependent upon the magnitude of the transmembrane pressure. Control of the transmembrane pressure, then, provides control over the rate of filtration across the membran;e.

Figure 1:
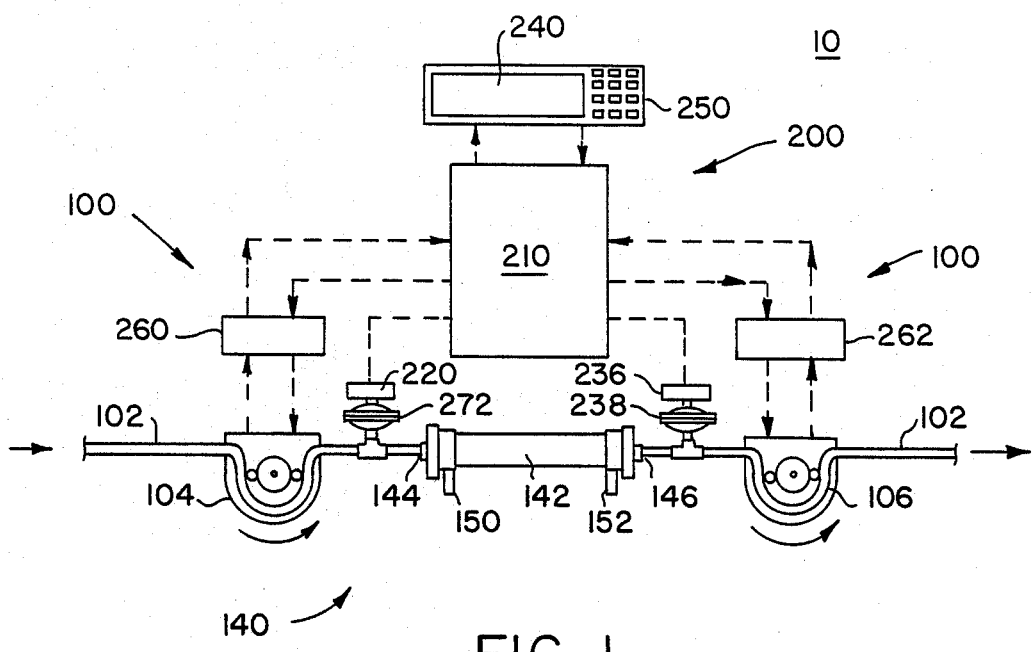
FIG. 1 illustrates a schematic diagram of an extracorporeal circulation apparatus employing principles of the invention.

Referring initially to FIG. 1, there is shown an extracorporeal circulation apparatus 10 structured in accordance with the principles of the present invention. The extracorporeal circulation apparatus 10 comprises a circulating means 100 for circulating blood through the apparatus, a treatment means 140 for treating the blood as it flows through the system, and a control system 200 for controlling the fluid pressure in the system.

The circulating means 100 includes tubing 102, an arterial pump 104, and a venous pump 106. The pumps 104, 106 can be standard peristaltic, or roller, pumps of the type widely used in blood treatment systems. One acceptable type of pump, employing spring-loading rollers, is Model SARA, manufactured by SARNS, of Ann Arbor, Michigan. The tubing 102 can be flexible plastic tubing also as ordinarily used in blood treatment apparatus and compatible with the pumps 104, 106. Such tubing 102 is typically from ⅛-inch to ⅜-inch in inner diameter, depending on the application and flow rate demands.

Figure 4:
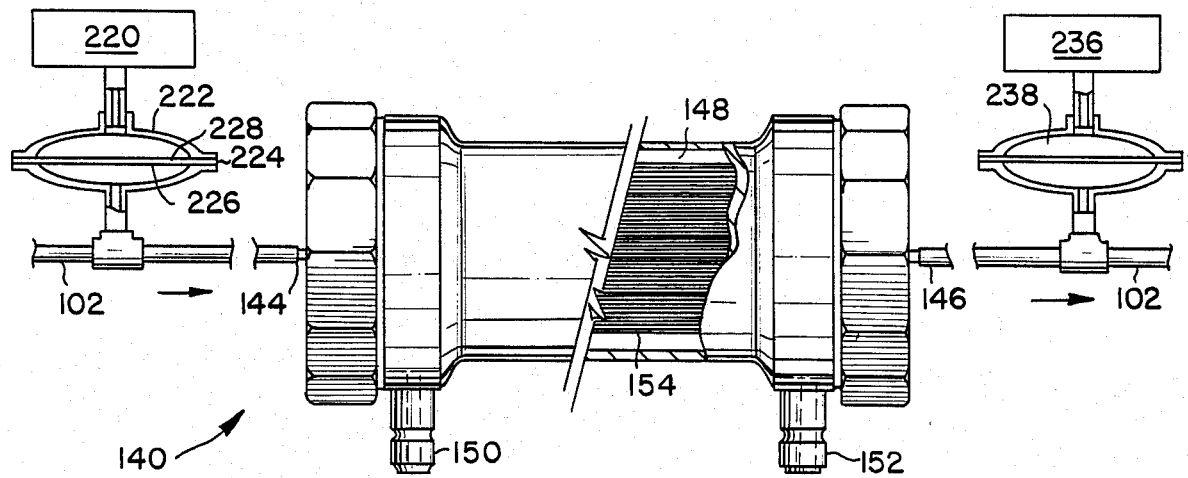
FIG. 4 illustrates an enlarged portion of the extracorporeal circulation apparatus of FIGS. 1, 2, and 3, showing the filter and pressure sensing elements.

With reference to FIG. 1 and to FIG. 4, the filter 142 includes a plurality of microporous or semipermeable membranes, such as hollow fibers 154, extending through and surrounded by an exterior chamber 148. The filter 142 can be of the standard hollow-fiber microporous membrane type, as typically used in dialysis and other applications, such as model TAF 12, made by Terumo, of Japan. A filter 142 of the hollow-fiber type is shown, but other suitable filters can be used. Filter 142 can be any appropriate filter means whose operating characteristics depend at least in part on inlet and outlet pressures including, but not limited to, flat-plate and coil filters utilizing microporous or semipermeable membranes. Cost and convenience, however, often favor use of a standard dialysis-type hollow-fiber filter. A filter inlet 144 and a filter outlet 146 are connected to tubing 102 of circulating means 100. The filter inlet 144 leads from the tubing 102 into the interior of hollow fibers 154. The exterior chamber 148 is normally sealed off from the outside of the filter 142 except via a chamber inlet 152 and a chamber outlet 150. The chamber inlet 152 and chamber outlet 150 typically serve as inlet and outlet, respectively, for dialysate fluid flowing through the exterior chamber 148 and around the hollow fibers 154 when the filter 142 is used, e.g., in two-needle dialysis with such dialysate flowing at a vacuum.

The control system 200 allows a technician, or other operator, to enter desired parameters for governing operation of the circulating means 100. The control system 200 includes a central processor 210 connected to two types of equipment—communication hardware and operational hardware. The communication hardware allows information to pass between the operator and central processor 210. The operational hardware allows the central processor 210 to monitor and control operation of the apparatus 10. The central processor 210 preferably comprises a digital microcomputer, such as a Zilog Z80 microcomputer, but alternatively may comprise an analog control apparatus, such as a mechanical or a pneumatic controller.

The communication hardware comprises an alphanumeric display 240 for communicating information from the central processor 210 to the operator, and a keypad 250 for communicating the information from the operator to the central processor 210. The alphanumeric display 240 may comprise a device capable of depicting 80 characters in two lines, such as a Model DE 280-1, manufactured by Digital Electronics Corp., of Hayward, Calif. The keypad 250 may comprise any keypad capable of communicating numeric or alphanumeric information to the central processor 210, such as a K0035 key pad, manufactured by DMC, of Pacific Palisades, California or Model 88JB2-E01, made by Grayhill, of LaGrange, Illinois. Alternatively, a cathode ray tube terminal, or a similar communication device, may be used. It may also be desirable to provide dedicated control elements as a further means for communicating information to the central processor 210.

The communication hardware primarily provides the extracorporeal circulation apparatus 10 with the initial parameters necessary to perform its processing function. The operator may provide input data through the keypad 250 or other control elements in response to queries from the central processor 210 via the alphanumeric display 240. In addition, the alphanumeric display 240 may also prompt the operator to adjust the settings of various clamps, valves, etc. for proper performance of the extracorporeal circulation apparatus 10. During operation of the apparatus 10, the central processor 210 may provide data on the alphanumeric display 240 in response to queries from the operator via the keypad 250 or control elements. Finally, the central processor 210 may provide warning messages or diagnostic information, as necessary, through the alphanumeric display 240.

The operational hardware is of two basic categories: transducers which communicate information to the central processor 210, and controllers which act in response to signals from the central processor 210. The transducers include an arterial pressure sensor 220, and a venous pressure sensor 236. The arterial and venous pressure sensors 220, 236 are located on either side of the filter 142 to detect the inlet and outlet pressure of fluid flowing through the tubing 102. For practical purposes, the arterial pressure sensor 220 reads the pressure at the filter inlet 144, and the venous pressure 236 reads pressure at the filter outlet 146. A pressure sensor suitable for use in both the arterial and venous positions is Model No. 142PC15G, manufactured by MicroSwitch-Honeywell, of Freeport, Ill. The controllers receiving signals from the central processor 210 include an arterial motor controller 260 and a venous motor controller 262, controlling the arterial pump 104 and the venous pump 106, respectively. A suitable motor controller is Model No. 110, manufactured by Power-UPS in Bohemia, N.Y. The central processor 210 can provide each motor controller 260, 262 with a digital angular velocity command, which will independently set the rotational speed and, hence, the pump rates of the arterial pump 104 and the venous roller pump 106.

In the descriptive material that follows, a commonly-numbered element appearing in various drawings depicts substantially the same device or feature wherever the element is pictured. Previous descriptions of that element, therefore, will generally apply where the element is referenced or pictured again, unless indicated otherwise.

Figure 2:
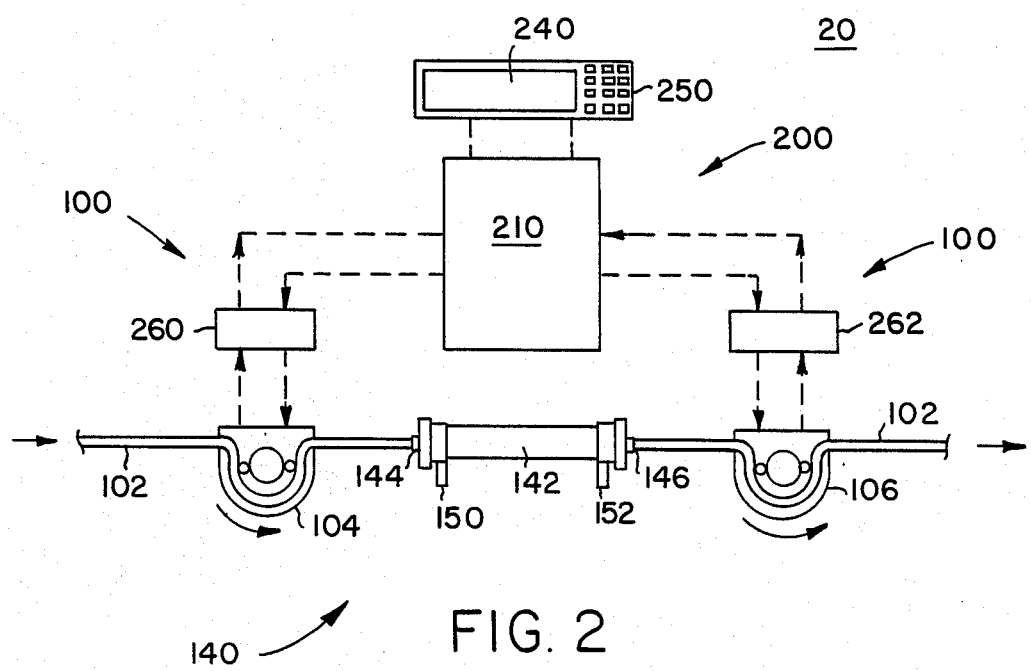
FIG. 2 illustrates a schematic diagram of another extracorporeal circulation apparatus employing principles of the invention.

FIG. 2 depicts another extracorporeal circulation apparatus 20 constructed in accordance with the present invention. Tubing 102 connects a treatment means 140 to an arterial pump 104 and a venous pump 106. A central processor 210, connected to an alphanumeric display 240 and a keypad 250, monitors and controls the speeds of the arterial pump 104 and the venous pump 106 via an arterial motor controller 260 and a venous motor controller 262, respectively. The extracorporeal circulation apparatus 20 depicted in FIG. 2 has no pressure snesors for the control means 210 to monitor pressure of blood flowing through the apparatus 20.

Figure 3:
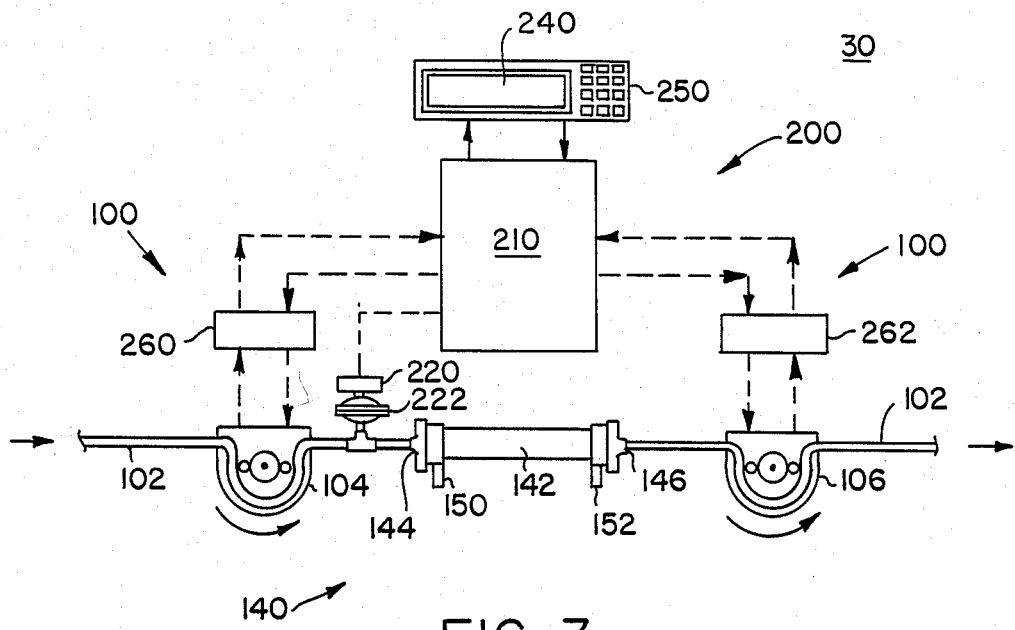
FIG. 3 illustrates a schematic diagram of a third extracorporeal circulation apparatus employing principles of the invention.

Referring now to FIG. 3, there is shown therein a third extracorporeal circulation apparatus 30 built according to the principles of the invention. Blood can flow through tubing 102, through an arterial pump 104, a treatment means 140, a venous pump 106, then out of the apparatus 30. An arterial motor controller 260 and a venous motor controller 262 relay signals between a central processor 210 and, respectively, the arterial pump 104 and the venous pump 106. An alphanumeric display 240 and a keypad 250 also act in relaying data between the central processor 210 and an operator. An arterial pressure sensor 220 detects the pressure of blood in the tubing 102 between the arterial pump 104 and the treatment means 140. The arterial pressure sensor 220 is connected for sending signals to the central processor 210.

FIG. 4 shows a more detailed view of the filter 142, the arterial pressure sensor 220, an isolator 222, the venous pressure sensor 236, and an isolator 238. Since each pressure sensor and isolator is like the other, it can be seen that a detailed description of the arterial pressure sensor 220 and isolator 22 will apply to and similarly describe the venous pressure sensor 236 and isolator 238. The arterial pressure sensor 220 indirectly, through the isolator 222, mesaures the pressure of the blood flowing within the tubing 102 at a point between the arterial pump 104 and the filter 142. Fluid pressure in the tubing 102 acts on the isolator 222 through the flow tee 230. A suitable pressure isolator is Model N2440, manufactured by Tri-Med, of Huntingdon Beach, Calif. The isolator 222 is primarily plastic and relatively inexpensive in contrast with the arterial pressure sensor 220. The fluid pressure through flow tee 230 bears against the diaphragm 224, on the lower side 226 of diaphragm 224. The diaphragm 224 is elastic, and flexes in response to the fluid pressure on its lower side 226. The diaphragm 224 thus flexes in response to the pressure of the fluid on the lower side 226 of the diaphragm 224 for transmission of pressure to the arterial pressure sensor 220. The diaphragm 224 is sealed along its edges with the housing of isolator 222 and is relatively impermeable, so as to prevent any flow of fluid around or through it. The transmitted pressure is then measured by the arterial pressure sensor 220. It can be seen, however, that fluid does not come into direct contact with the arterial pressure sensor 220. After use, the inexpensive isolator 222 is discarded and replaced. The more costly electronic arterial pressure sensor 220 can be re-used for another patient, since it remains free of contamination by the fluid being processed.

OPERATION OF THE APPARATUS

In general terms, blood to be treated flows from a source, into the inlet of the arterial pump 104, through the treatment means 140, then through the venous pump 106 and out of the extracorporeal circulation apparatus 10. The central processor 210 maintains the flow rate of blood through the arterial and venous pumps 104, 106 so as to provide a predetermined flow rate of fluid exiting the extracorporeal circulation apparatus 10 and, simultaneously, to establish either a predetermined interior or transmembrane pressure in the treatment means, or a predetermined rate of filtration when the treatment means 140 includes a filter such as filter 142.

Initially, the operator supplies the central processor 210 with the desired operational parameters, setting the output flow rate and the interior or transmembrane pressure, or filtration rate. The central processor 210 determines from the operational parameters the requisite rotational speed of the venous and arterial pumps 104, 106. The central processor 210 continuously monitors the venous and arterial pressures and pump rates to verify that the desired interior or transmembrane pressure, or filtration rate, is being achieved. The operator can subsequently input into the keypad 250 a different desired output flow rate. The central processor 210 compensates for deviations from the desired pressure or filtration rate by adjusting only the rotational speed of the arterial pump 104, while holding the venous pump 106 at the selected output rate.

More particularly, as applied to the treatment means 140 having a filter 142, the rate of filtration of components through the membrane is proportional to the transmembrane pressure. The transmembrane pressure at any point is the difference between the membrane interior and exterior pressures. For simplicity, the membrane exterior stays constantly and uniformly at substantially atmospheric pressure. The transmembrane pressure then depends solely on the interior pressure of the hollow fibers 154. Friction causes the pressure of the blood to drop continually as it flows from the filter inlet 144 to the filter outlet 146. The membrane interior pressure lies at all times between the inlet pressure and the outlet pressure of the filter 142, and is a function of those inlet and outlet pressures. The exact rate of filtrate removal, then, depends upon the flow characteristics of the filter 142 used, as well as the filter inlet 144 and filter outlet 146 pressures.

Employing the extracorporeal circulation apparatus 10 shown in FIG. 1, the operator enters values for the desired output flow rate and the preferred average transmembrane pressure into the keypad 250, prompted as necessary by the alphanumeric display 240. The extracorporeal circulation apparatus 10 is connected so as to treat blood flowing from and returning to a patient. In some applications, means for accumulating blood upstream of the arterial pump 104 is necessary to allow an occasional arterial pump rate faster than the patient's circulatory system can deliver, or for storage of blood until enough accumulates to operate the apparatus. The output flow rate is limited by the flow rate at which the patient can receive returned blood if there is no accumulation device between the venous pump and the patient, and also by the maximum rate allowable without hemolyzing red cells. The average transmembrane pressure is determined by the treatment to be performed, the undesirable components to be removed, the rate of filtration desired, and any other relevant variables called for by the particular treatment means 140 employed. The keypad 250 transmits the input parameters to the central processor 210. The central processor 210 continually reads the pressure data transmitted by the arterial pressure sensor 220 and the venous pressure sensor 236.

Since the pressure of blood flowing through the hollow fiber 154 varies linearly with the distance from the filter inlet 144 (i.e., constant flow causes a constant rate of pressure drop in the blood flowing through the filter 142), the average transmembrane pressure is assumed to be the average of the two pressures measured by pressure sensors 220, 236. The central processor 210 automatically calculates the average transmembrane pressure accordingly. If the calculated average transmembrane pressure is too low, the central processor 210 responds by signalling the arterial motor controller 260 to speed up the arterial pump 104. The rate of the venous pump 106, however, remains steady, keeping the output flow rate exiting the treatment means 140 constant until the operator selects a different rate. Conversely, if the average transmembrane pressure is too high, the central processor 210 has the arterial motor controller 260 slow down the arterial pump 104, while the venous pump 106 output rate remains unchanged unless the operator selects a new rate. Venous motor controller 262 adjusts the speed of venous pump 106 as necessary to ensure the outflow parameter set by the operator is being achieved. In this manner, the central processor 210 periodically monitors the flowing pressures detected by the sensors 220, 236 and adjusts the arterial pump 104 rate to maintain the desired average transmembrane pressure, while the output flow rate is held at the desired level.

The relationship between the flow rate through a roller pump and the rotational speed of that roller pump may theoretically be expressed as follows:

$$Flow = SV \times 2 \times V$$

where:
SV = Stroke Volume (Volume pumped in ½ revolution of rollers)
V = Speed of Pump (RPM)

This relationship between flow rate and pump speed is generally accurate for fully occluding pumps, at speeds at which tubing resiliency and the like do not affect pump performance. This relationship also applies to standard partially occluding pumps, when properly calibrated, in which the formula given is accurate to within ±5%, up to 900–1000 mm. of mercury.

The average transmembrane pressure can be set at an elevated level, and the central processor 210 regulates the extracorporeal circulation apparatus 10 keeping the average transmembrane pressure substantially at the desired level free of limitation by the patient's blood pressure, the blood flow rate, or the need to avoid hemolysis of red cells. The invention thus provides means for raising transmembrane pressure above that obtainable with only one pump, without the drawbacks imposed by a partially occluding device downstream of the filter 142. The venous pump 106 induces much less hemolysis in the flowing blood than does a partially occluding device. As described previously, pump rollers cause some hemolysis, particularly if fully occluded. A roller, however, hemolyze cells only near the point of contact with the tubing 102. As the roller traverses the tubing 102 in the venous pump 106, blood upstream is at a different pressure from the blood downstream of the roller. As the roller completes a pump cycle, the roller disengages from and releases the tubing 102, and the pressures equalize. Upstream blood as far back as the next succeeding roller will attain the same pressure as blood downstream of the now-disengaged roller. The pressure change thus extends along the length of tubing 102 extending upstream to the next roller. The pressure gradient with respect to the length of flowpath, then, is less than for a single point of occlusion, where the pressure change occurs over an extremely short interval of tubing 102. Hemolyzing shear stress is proportional to this pressure gradient. The venous pump 106 thus achieves pressure changes with significantly less damage to blood than that caused by an occluding device. Moreover, whereas a device partially occluding the flow allows pressure downstream to affect pressure upstream, the venous pump 106 isolates upstream and downstream pressures, especially when the venous pump 106 fully occludes the tubing 102. The transmembrane pressure thus can be regulated without interference from pressure and conditions downstream of the venous pump 106. The venous pump 106, moreover, can raise or lower the pressure of flowing blood, whereas a partially occluding device can only lower the pressure. Lastly, in contrast to an apparatus utilizing a vacuum to increase transmembrane pressure, the invention generates necessary transmembrane pressure free of attendant complexity, unreliability, and difficulty of control resulting from use of a vacuum-assisted apparatus.

Referring now to FIG. 2, the extracorporeal circulation apparatus 20 can be set to control more directly the desired rate of fluid removal through the membrane walls of the filter 142, as opposed to controlling the transmembrane pressure across the membrane walls, as for the apparatus 10 shown in FIG. 1. The operator specifies the output flow rate and the desired net filtration rate, entering them into the keypad 250. These values are transmitted to the central processor 210. The arterial motor controller 260 and the venous motor controller 262 transmit data regarding the speeds of the arterial pump 104 and the venous pump 106, respectively. The central processor 210 monitors the pump speeds and calculates the resultant flow rates.

The central processor 210 subtracts the flow rate of the venous pump 106 from the rate of the arterial pump 104. The net filtration rate through the membrane walls of the filter 142 is the difference between the flow rates of the arterial pump 104 and the venous pump 106. If the operator alters the desired filtration rate, the central processor 210 adjusts the speed of the arterial pump 104 as needed, while maintaining the venous pump 106 at the specified output flow rate. If the new desired filtration rate is higher than before, the central processor 210 speeds up the arterial pump through the arterial motor controller 260. Similarly, if the new filtration rate is lower than previously, the central processor 210 signals the arterial motor controller 260 to reduce the rate of the arterial pump 104.

The present invention, therefore, further provides a reliable, precise means for predicting, determining, and regulating the rate of filtration of components through the membrane walls of the filter 142. Prior art apparatus have failed to provide means for continually monitoring and controlling the component filtration rate with such a degree of precision and regularity. The present invention provides an apparatus for directly measuring and regulating filtration rates. This capability provides a powerful tool for predicting and monitoring a variety of medical procedures, including autotransfusion, dialysis, plasmapheresis, and other treatment methods.

Referring to FIG. 3, the extracorporeal circulation apparatus 30 depicted there is suited for possible applications demanding more sensitive pressure regulation of blood flow through the treatment means 140. The pressure of the blood at any point within the treatment means 140 depends on the inlet pressure at inlet 144, the flow rate of the blood through the treatment means 140, and the permeability of the treatment means 140. The relationship between such interior pressure within the treatment means 140 on one hand, and the flow rate and the inlet pressure, on the other, can be determined for any treatment means 140 of known permeability. Controlling the inlet pressure at inlet 144 thus indirectly controls the interior pressure for any constant flow rate and any known treatment means 140. The operator enters the desired interior pressure and chosen output flow rate into the keypad 250. The keypad 250 relays these entered data to the central processor 210. The operator can also enter permeability and performance data regarding the treatment means 140.

The central processor 210 calculates the proper inlet pressure needed for the interior pressure sought. The central processor 210 keeps the venous pump 106 running at the desired output flow rate. The central processor 210 compares the pressure measured by the arterial pressure sensor 220 with the calculated proper inlet pressure. If the pressure at the arterial pressure sensor 220 is not correct, the central processor 210 adjusts the rate of the arterial pump 104. To increase the pressure at the arterial pressure sensor 220, the rate of the arterial pump 104 is increased. If the pressure at the arterial pressure sensor 220 is too high, the central processor 210 will signal the arterial motor controller 260 to reduce the speed of the arterial pump 104. At all times, the venous pump 106 output flow rate is maintained at the selected outflow rate, until the operator enters a new desired outflow rate into the keypad 250.

For apparatus built in accordance with the principles of the invention and intended to remove or filter undesirable components from the blood being treated, the arterial pump 104 must pump at least as fast as the venous pump 106 to prevent a vacuum from occurring in the interior of the treatment means 140. If the arterial pump 106 output were less than the venous pump 104 output, the amount of blood flowing from the arterial pump 104 alone would be less than that needed to supply the required input to the venous pump 106. To make up for the lack of input fluid, liquid or gas within the exterior chamber 148 would flow through the membrane walls, into the interior of the treatment means 140, into the blood being treated, and then to the venous pump 106. To prevent such reverse flow across the membrane walls, the output of the arterial pump 104 must be at least as great as that of the venous pump 106. Since the flow of blood from the arterial pump 104 to the venous pump 106 causes the fluid pressure to drop steadily, the arterial pump 104 must in fact flow faster than the venous pump 106.

The present invention can also provide for adding desired components to blood. Operation of the apparatus embodying the invention would then create a transmembrane pressure tending to force such desired components, external to a membrane, through that membrane to mix with blood in the space enclosed by the membrane. To achieve such a transmembrane pressure resulting in absorption of components by the blood, the venous pump 106 output would have to be no less than the arterial pump 104 output, to prevent outflow into the exterior chamber of the treatment means 140. In providing absorption of components by the blood, the apparatus would be operated generally similarly to the manner previously described, with parameters modified as appropriate.

AUTOTRANSFUSION APPARATUS

Autotransfusion of a patient's own blood during surgery provides various benefits. It minimizes the need for transfusing units of blood obtained from a blood bank for transfusions. Such stored blood can be scarce and expensive. Blood matching the recipient's blood type may be in short supply. Moreover, transfusion of stored blood may subject the recipient to unknown risks of disease due to undetected contaminants or defects in the stored blood. Thus, there is a distinct advantage in cleansing the patient's contaminated blood during the operation and retransfusing it into the patient's circulatory system.

One type of prior art autotransfusion apparatus includes a vacuum-assisted filter with a single pump, with the advantages of compact size, portability, and relative ease of use, all making it suitable for operating room environment applications. It has, however, the inherent disadvantage of controlling the vacuum. Prior art apparatus in general use alos suffers from a low degree of safety, since the bubble detector can be manually disarmed.

Another prior art autotransfusion apparatus, intended for operating-room use, employs a centrifuge to separate red cells from the rest of the blood. Whole blood flows from an inlet pump into a centrifuge chamber. Red cells, due to their density, collect outermost on the walls of the chamber. Undesirable components, together with valuable plasma, platelets, and white blood cells, collect in the inner region of the chamber and are discarded. The red blood cells are mixed with necessary new elements and pumped back to the patient. A significant problem with using this simple centrifuge apparatus is the resultant waste of the patient's other usable and valuable blood components. Moreover, the problem of potential contamination from foreign blood components is still present. Original red blood cells are returned to the patient, but additional elements must come from outside sources, including those carrying risks of disease. Another kind of prior art centrifuge apparatus does allow separation and recovery of various components of the blood besides red cells, including white cells, platelets, and plasma. This apparatus, however, is bulky, intricate, and complex in operation. It utilizes optical sensing of components discharged from the centrifuge as the blood is spinning. Drawing components from the center of the centrifuge as they accumulate, the least dense components are first withdrawn, progressing through the components of increasing density, until red cells are finally collected. As the apparatus senses changes in optical characteristics of the withdrawn elements, it diverts the flow from the centrifuge to the appropriate receptacle. The complexity and size of the equipment constituting this centrifuge apparatus make it wholly inappropriate for the operating-room environment. Both types of centrifuge apparatus described above require trained specialist operators. They are labor-intensive, expensive machines to use. Both are completely inappropriate machines, moreover, for use in many emergency rooms, where time, space, and specialists are all in short supply.

Figure 5:
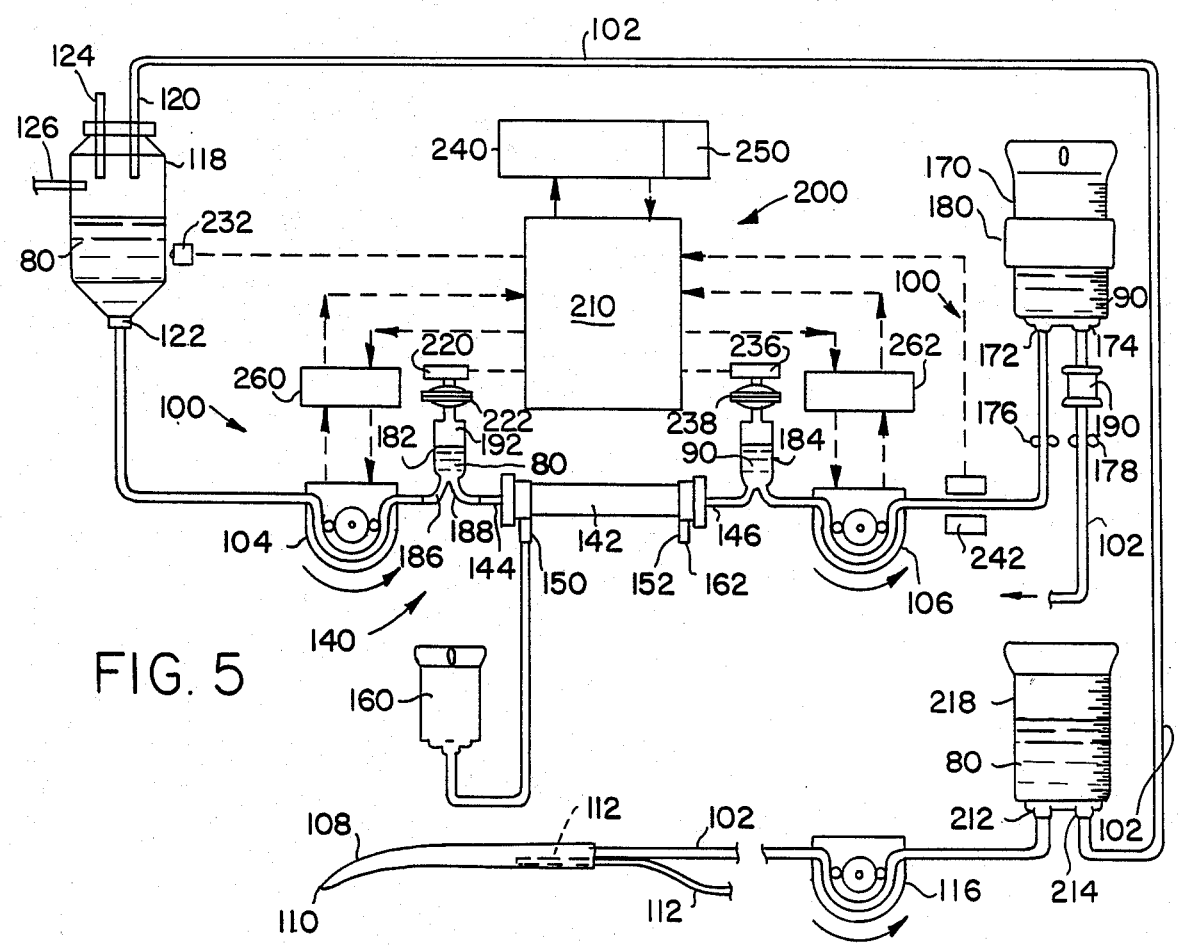
FIG. 5 illustrates a schematic diagram of an autotransfusion apparatus employing principles of the invention.

Depicted in FIG. 5 is an autotransfusion apparatus 40 constructed in accordance with the principles of the invention. The circulating means 100 of the autotransfusion apparatus 40 also includes a suction wand 108 for initial intake of whole blood 80 from a surgical field. A suitable suction wand 108 is model BDS-100, manufactured by Bentley, of California. The suction wand 108 includes an open suction tip 110 leading into the interior of the hollow suction wand 108. The suction wand 108 is of a size and shape so as to be manipulable by a surgeon in the course of an operation. A collection pump 116, described in more detail below, operates a partial vacuum within the interior of the suction wand 108. Vacuum inside the suction wand 108 allows the surgeon to gather whole blood 80 through the suction tip 110 into the interior of the suction wand 108 during the operation. The suction wand 108 may further include a smaller-diameter anticoagulant tube 112. The anticoagulant tube 112 may be located inside the suction wand 108, as shown in FIG. 5, or its open end might be outside the suction wand 108 and adjacent to the suction tip 110. In either case the anticoagulant tube 112 must be situated so that anticoagulant flowing from an anticoagulant source (not shown) is drawn by the vacuum inside the suction wand 108 to mix with the whole blood 80 flowign into the autotransfusion apparatus 40. The anticoagulant is provided to reduce clotting of blood. A suitable anticoagulant for use in the autotransfusion apparatus 40 is Heparin, made by Upjohn, of Michigan. In addition, although the anticoagulant tube 112 is shown in FIG. 5 as part of a double-lumen suction wand 108, anticoagulant could mix with the whole blood 80 further downstream.

Tubing 102 connected to the suction wand 108 leads to the collection pump 116. The collection pump 116 may be a roller pump, like the arterial and venous pumps 104, 106. The collection pump 116 can be set to run continuously or to be actuated only when the operator desires to collect whole blood 80 with the suction wand 108. From the collection pump 116 tubing 102 connects to the inlet 212 of an input accumulator 218. The input accumulator 218 is a collapsible bag, with graduations marked to indicate the volume of fluid contained therein.

Initially, the input accumulator outlet 214 is sealed. To flow whole blood 80 through the autotransfusion apparatus 40, the outlet 214 is punctured and joined with tubing 102 connected to a cardiotomy inlet 120 leading into a cardiotomy 118. The cardiotomy 118 includes a simple filter for catching gross contaminants. The cardiotomy 118 can be a collapsible bag if used in conjunction with a roller collection pump 116 and a collapsible input accumulator 218. For use with a roller collection pump 116, the cardiotomy 118 includes a cardiotomy vent 124 which is open to the atmosphere to release trapped air. Alternatively, a vacuum source (not shown) can be connected to a vacuum port 126 on the cardiotomy. Such a vacuum source then can provide suction for collecting whole blood 80 with the suction wand 108, in place of the collection pump 116. If a vacuum source is so utilized for gathering blood, the cardiotomy 118 must be a rigid container to withstand collapse; the input accumulator 218 must likewise be rigid, or else not included. An acceptable rigid cardiotomy 118 is Model BCR-3000, made by Bentley, of California. When using a vacuum source, all other openings to atmosphere in the cardiotomy 118, including the cardiotomy vent 124, must be sealed.

Another portion of tubing 102 leads from the cardiotomy outlet 122 to the inlet of the arterial pump 104. Tubing 102 connects the arterial pump 104 to a sealed arterial compliance chamber 182 between the arterial pump 104 and the filter 142. The base of the arterial compliance chamber 182 has a compliance chamber inlet 186 and a compliance chamber outlet 188. During operation, a quantity of whole blood 80 fills a lower portion of the arterial compliance chamber 182, and an air cushion 192 is maintained above the whole blood 80. A pressure vent 194 at the top of the arterial compliance chamber 182 transmits pressure in the air cushion 192 to the arterial pressure sensor 220 via the arterial pressure isolator 222. The arterial compliance chamber 182 serves, firstly, as a debubbler by providing a receptacle for air to bubble out of the flowing whole blood 80 into the air cushion 192. Secondly, the arterial compliance chamber 182 helps smooth the time profile of pressure measured by the arterial and venous pressure sensors 220, 236. Roller pumps create high and low pressure "spikes" as each roller first contacts, then disengages, tubing 102. The air cushion 192 absorbs these pressure spikes to some degree, resulting in a smoother pressure signal to be transmitted to the central processor 210. The smoother signal facilitates interpretation and use of the pressure data by the central processor 210. An acceptable type of arterial compliance chamber 182 is included in standard dialysis sets available from Renal Systems, of Minneapolis, Minn.

Tubing 102 leads from the arterial compliance chamber outlet 188 to the filter inlet 144, and from the filter outlet 146 to the venous compliance chamber 184. The description of the arterial compliance chamber 182 applies to and similarly describes the venous compliance chamber 184. Tubing 102 then connects the outlet of the venous compliance chamber 184 to the venous pump 106. The arterial pump 104 and venous pump 106 are roller pumps, as described previously. The filter 142 is a hollow-fiber microporous membrane filter. A plug 162 seals the chamber inlet 152. A collection bag 160 is connected to the chamber outlet 150 of the filter 142. The collection bag 160 can be any appropriate bag for accumulating fluids removed from blood flowing through the filter 142.

The outlet of the venous pump 106 joins tubing 102 connected to a reinfusion bag 170. The reinfusion bag 170 can be a common collapsible bag like the type used as the cardiotomy 118 when a collection pump 116 provides the vacuum necessary for collecting whole blood 80. A pressure cuff 180 surrounds the reinfusion bag 170 to provide means for pressuring the reinfusion bag 170. The pressure cuff 180 is an inflatable bag that can wrap around another object in a doughnut-like fashion. Inflating the pressure cuff 180 applies pressure to the surrounded object, in this case the reinfusion bag 170; deflating the pressure cuff 180 relieves pressure. The pressure cuff 180 can be designed for manual operation, or it can be a power cuff for automatic operation.

A final portion of tubing 102 joins the reinfusion bag outlet 174 with the return circuit to the patient. An outlet filter 190 in the circuit provides final cleansing of impurities from the filtered blood 90. One acceptable outlet filter 190 is Model 4C2423, manufactured by Travenol, of Illinois. A reinfusion inlet clamp 176 and a reinfusion outlet clamp 178 attach to those portions of tubing 102 that lead into and out of the reinfusion bag 170. These clamps 176, 178 can be standard, manually operated roller valves if the reinfusion bag 170 is to be directly attached by an operator. Such roller valves are mounted on the tubing and include rollers that can pinch the tubing to obstruct flow, or can be rolled away to permit full flow. For automatic operation, electrically controlled valves can alternately open and close the flow to and from the reinfusion bag 170. A suitable automatic valve can be manufactured from a rotary solenoid such as model 58210-31, manufactured by Ledex, of Vandalia, Ohio.

The control system 200 of the autotransfusion apparatus 40 includes a central processor 210, an arterial pressure sensor 220, a venous pressure sensor 236, an arterial motor controller 260, a venous motor controller 262, a keypad 250, and an alphanumeric display 240, substantially as previously described. In addition, the control system 200 also includes a cardiotomy level detector 232. The level detector 232 monitors the presence or absence of whole blood 80 at a pre-set level within the cardiotomy 118. The level detector 232 can employ mechanical, optical, capacitive, ultrasonic, or any other suitable means to monitor blood, but an optical sensor provides a preferred combination of reliability and economy. The level detector 232 provides a digital electric signal indicative of the presence or absence of detected fluid. A suitable level detector is Model S22104, manufactured by Skan-A-Matic, of Elbridge, N.Y.

The control system 200 further includes a bubble detector 242. The bubble detector 242 uses ultrasonic or other adequate means for detecting air or other gas bubbles that may be entrained in the filtered blood 90 travelling from the venous pump 106 to the reinfusion bag 170. Upon detecting bubbles, the bubble detector 242 can send an appropriate digital signal to the central processor 210. An acceptable bubble detector is Model RS 3300, made by Renal Systems, of Minneapolis, Minn.

The bubble detector 242 cannot be manually bypassed or disarmed. Before the autotransfusion apparatus 40 begins operating, the bubble detector 242 is already in a disarmed state. The operator can thus start the autotransfusion apparatus 40 without having to bypass the bubble detector 242. As priming fluid or filtered blood 90 flows past the bubble detector 242 for the first time, the bubble detector 242 signals the central processor 210 regarding the detected presence of fluid. The central processor 210 then automatically arms the bubble detector 242. Once armed, the bubble detector 242 can signal the central processor 210 again upon sensing bubbles entrained within the filtered blood 90. Since the bubble detector 242 cannot be disarmed, the invention provides another sure, dependable level of safety preventing infusion of the patient with gas. This enhanced safety is not dependent on human action, since the bubble detector 242 automatically arms itself without attention from the operator.

Optionally, the autotransfusion apparatus 40 can be designed for direct withdrawal or gathering of whole blood 80 from a patient and automatic delivery of filtered blood 90 to the patient from the reinfusion bag 170. The cardiotomy 118 could be deleted or bypassed if the gathered whole blood 80 is sufficiently clean for filtering. Further, the automatic control system can include a level detector (not shown) to monitor the level in the reinfusion bag 170, or a pressure sensor (not shown) to measure the pressure of filtered blood 90 flowing between the venous pump 106 and the reinfusion bag 170. The reinfusion bag 170 level detector can be similar to the cardiotomy level detector 232; the reinfusion bag 170 pressure sensor can be like the arterial and venous pressure sensors 220, 236.

OPERATION OF THE AUTOTRANFUSION APPARATUS

Referring generally to FIG. 5, whole blood 80 enters the autotransfusion apparatus 40 through use of the suction wand 108 by an operator. Whole blood 80 collects in the input accumulator 218. After enough whole blood 80 is collected, the input accumulator outlet 214 is connected to the tubing 102 leading to the cardiotomy 118. The arterial pump 104 pumps the whole blood 80 from the cardiotomy 118 into the interior of the hollow fibers 154 of the filter 142. The control system 200 regulates the operation of the autotransfusion apparatus 40, in accordance with the principles of the invention, to control outflow and optimize transmembrane filtration. Referring also to FIG. 4, the separated components exit the filter exterior chamber 148 through the chamber outlet 150 into the collection bag 160. The venous pump 106 pumps the remaining filtered blood 90 into the reinfusion bag 170 while the reinfusion outlet clamp 178 is closed. After enough filtered blood 90 has accumulated, the reinfusion inlet clamp 176 closes and the reinfusion outlet clamp 178 opens. A pressure cuff 180 around the reinfusion bag 170 inflates to apply pressure to the reinfusion bag 170 to force the filtered blood 90 back to the patient at an acceptable speed. After the reinfusion bag 170 empties, the reinfusion outlet clamp 178 closes, the pressure cuff 180 deflates, the reinfusion inlet clamp 176 opens, and the filtered blood 90 can again fill the reinfusion bag 170.

Referring in more detail still to FIG. 5, the operator uses the suction wand 108 to gather whole blood 80 as desired from the surgical field. Whole blood 80 enters the suction tip 110, mixes with the anticoagulant, and then flows into the tubing 102 of the autotransfusion apparatus 40. Whole blood 80 flows through the tubing 102 and fills the input accumulator 218. Since the input accumulator outlet 214 is initially sealed, the whole blood 80 does not yet contact or contaminate the remainder of the autotransfusion apparatus 40. If insufficient whole blood 80 is collected to warrant retransfusion, the operator can choose to discard the whole blood 80 and the input accumulator 218. In that case, only those elements of the apparatus 40 from the suction tip 110 to the input accumulator outlet 214 are contaminated by the whole blood 80. Once the operator decides to treat the whole blood 80, the input accumulator outlet 214 is punctured and connected to tubing 102 leading to the cardiotomy inlet 120. Whole blood 890 then can flow into the cardiotomy 118, and into the remainder of the autotransfusion apparatus 40.

Entrained air within the whole blood 80 sitting in the cardiotomy 118 can bubble out and escape to the atmosphere through the cardiotomy vent 124. Whole blood 80 then flows from the cardiotomy 118 through the cardiotomy outlet 212 into the tubing 102. Whole blood 80 at the inlet of the arterial pump 104 is, for practical purposes, at atmospheric pressure. The arterial pump 104 pumps whole blood 80 through the tubing 102 into the filter 142. The arterial pump 104 elevates the pressure of the blood by pumping. Referring also to FIG. 4, the exterior chamber 148 remains at atmospheric pressure. The fluid pressure inside the hollow fibers 154 thus exceeds the atmospheric pressure outside, in the exterior chamber 148. This transmembrane pressure forces fluids and components smaller than the pores in the microporous membrane to flow outward into the exterior chamber 148. These removed components then flow from the exterior chamber 148, through the chamber outlet 150, into the collection bag 160. The remaining blood components—calls, larger proteins, and fluid—exit the hollow fibers 154, flowing through the filter outlet 146 back to the tubing 102. Filtered blood 90 flows from the filter 142 to the venous pump 106. The venous pump 106 pumps filtered blood 90 into the reinfusion bag 170 via the reinfusion bag inlet 172. When the reinfusion bag 170 is full, the filtered blood 90 is returned to the patient. To return this filtered blood 90, the circulating means 100 is shut off, the reinfusion inlet clamp 176 closes, and the reinfusion outlet clamp 178 opens. The pressure cuff 180 is inflated to pressurize the reinfusion bag 170 to expedite return of filtered blood 90. After filtered blood 90 exists the reinfusion bag 170, it flows through an outlet filter 190 for final removal of impurities and returns to the patient. The pressure cuff 180, the reinfusion inlet clamp 176, and the reinfusion outlet clamp 178 can be operated manually. Optionally, a level sensor or a reinfusion pressure sensor can be included to provide automatic operation of the clamps 176, 178 and the pressure cuff 180. If using a level sensor, the blood level rises in the reinfusion bag 170 until it is detected. The level sensor then activates the return flow to the patient. Alternatively, a reinfusion pressure sensor can similarly activate the return flow when the pressure downstream of the venous pump 106 reaches a pre-set maximum value.

An operator normally would normally cycle the autotransfusion apparatus 40 on and off, as desired. Optionally, it could automatically cycle in response to levels detected in the cardiotomy 118. The autotransfusion apparatus 40 include safety devices to minimize the risk of accidentally pumping air into a patient's cardiovascular system. The level detector 232 in the cardiotomy 118 provides an initial level of safety. If the level of whole blood 80 in the cardiotomy 118 drops below a safe point, the level detector 232 transmits a signal to the central processor 210. The central processor 210 immediately signals the motor controllers 260, 262 to shut off the arterial pump 104 and the venous pump 106. The bubble detector 242 provides an additional level of safety. Before priming fluid or filtered blood 90 first flows through the autotranfusion apparatus 40, the bubble detector 242 allows the apparatus 40 to operate normally. Upon first detecting fluid, the bubble detector 242 signals the central processor 210. The central processor 210 then "arms" the bubble detector 242. Continued functioning of the apparatus 40 requires an absence of bubbles flowing past the bubble detector 242. The bubble detector 242 monitors the filtered blood 90 flowing through the tubing 102 toward the reinfusion bag 170. Any gas that might accumulate in the reinfusion bag 170 creates a risk of injecting such gas into the patient. If air or other gas bubbles are detected, the bubble detector 242 signals the central processor 210. The central processor 210 again immediately turns off the arterial pump 104 and venous pump 106 to prevent pumping gas into the reinfusion bag 170.

In unusual situations, it may be desirable to autotransfuse blood immediately and directly to a patient. To avoid delay, any or all of the blood accumular devices—including the input accumulator 218, the cardiotomy 118, and the reinfusion bag 170 and associated clamps 176, 178—can be eliminated from the autotransfusion apparatus 40. Whole blood 80 is collected and drawn directly into the tubing 102 leading to the arterial pump 104. Filtered blood 90 then flows from the venous pump 106, through the tubing 102, the bubble detector 242, the outlet filter 190, and then directly back to the patient. Such a hookup simplifies the system and returns blood faster. This increase in speed, though, is at the expense of a slightly reduced response time available to the central processor 210 to turn off the pumps 104, 106, should the bubble detector 242 detect gas within the filtered blood 90 returning to the patient.

TWO-NEEDLE DIALYSIS APPARATUS

Figure 6:
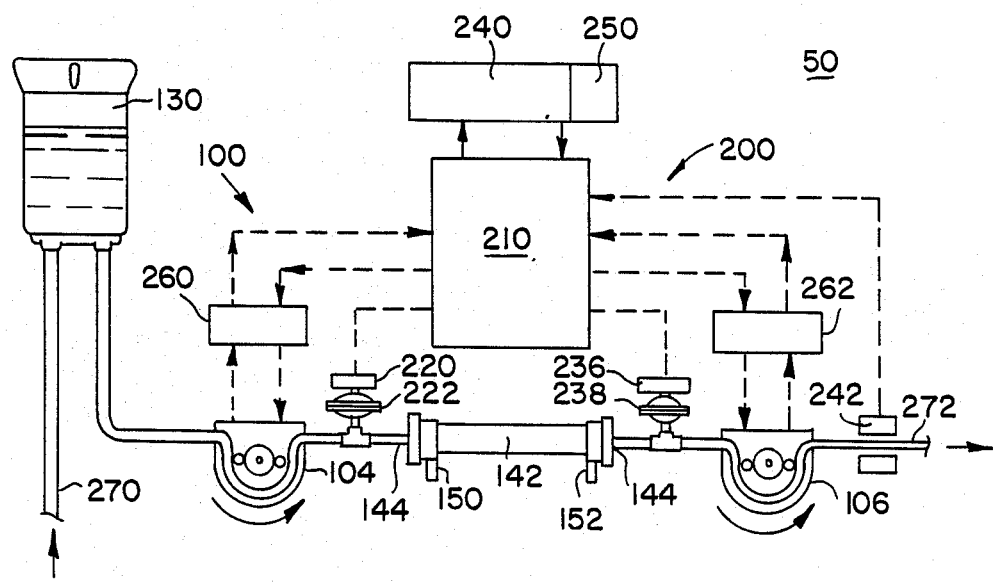
FIG. 6 illustrates a schematic diagram of a conventional, two-needle dialysis system employing principles of the invention.

Referring now to FIG. 6, there is shown therein a two-needle dialysis apparatus 50 constructed in accordance with the principles of the invention. In the two-needle dialysis apparatus 50, blood flows from the patient through an inlet 270, through the dialysis circuit for treatment, accumulates in a dialysis inlet bag 130 bag, flows through the arterial pump 104, the filter 142, and the venous pump 108, then returns through an outlet 272. The central processor 210 monitors and regulates the arterial and venous pump 104, 106 speeds, the arterial and venous pressure sensors 220, 236 (if included), and the bubble detector 242, in a manner generally as described for the extracorporeal circulatoin apparatus 10, 20, or 30, and autotransfusion apparatus 40, to achieve a desired transmembrane pressure or a selected fluid removal rate, at a specified discharge rate of filtered blood 90 returning directly to the patient from the venous pump 106. Optionally, the two-needle dialysis apparatus 50 can be constructed without the inlet bag 130 for accumulating whole blood 80. The inlet bag 130 ensures that there will be an adequate supply of whole blood 80 for the arterial pump 104 to be able to pump faster, thereby increasing the pressure inside the fibers 154, without exhausing such supply. If the patient, however, can provide an adequate blood flow directly, the inlet bag 130 can be eliminated from the two-needle dialysis apparatus 50. Eliminating the inlet bag 130 reduces the quantity of the patient's blood stored outside the body, and is therefore preferred, if possible.

As described previously for prior art, conventional dialysis, dialysate fluid can be flowed through the exterior chamber 148, into the chamber inlet 152 and out the chamber outlet 150. Unlike conventional dialysis, however, no vacuum is necessary, with or without dialysate fluid. The ability to elevate and control the pressure inside the hollow fibers 154 obviates any need for a vacuum in the exterior chamber 148. Absent the need for this vacuum, regulation of the dialysis process is thus simpler and more reliable than in the conventional apparatus.

SINGLE-NEEDLE DIALYSIS APPARATUS

Figure 7:
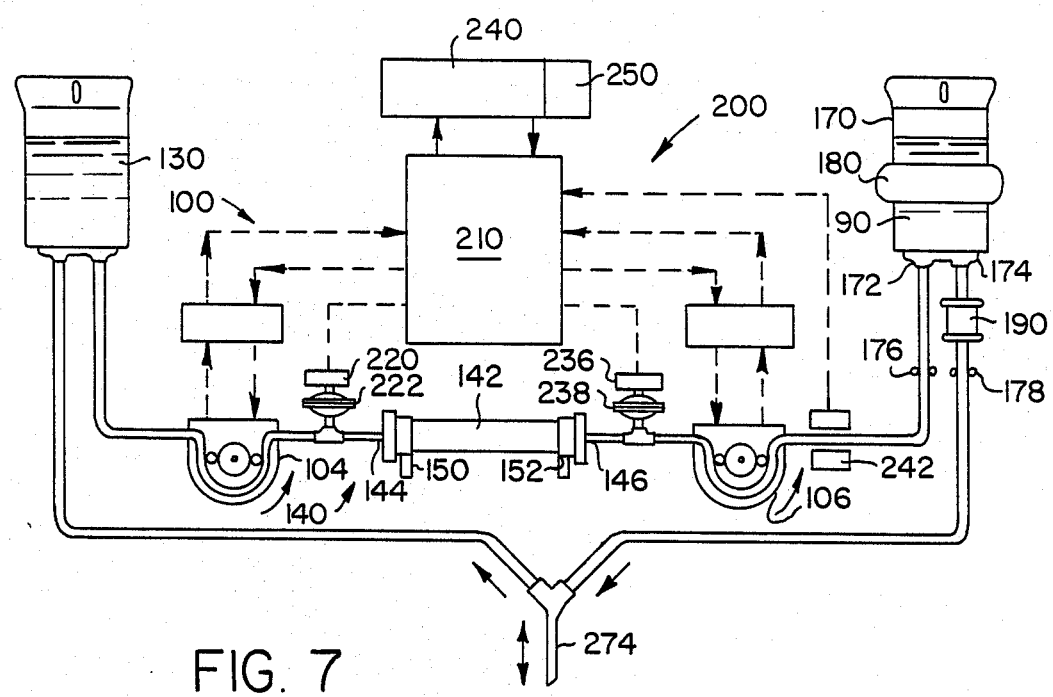
FIG. 7 illustrates a schematic diagram of a single-needle dialysis system employing principles of the invention.

Referring now to FIG. 7, there is shown a single-needle dialysis apparatus 60 constructed in accordance with the principles of the invention. Whole blood 80 flows from the patient, and filtered blood 90 alternately returns to the patient through the inlet/outlet needle 274. Whole blood 80 flows from the patient and accumulates in the dialysis inlet bag 130. The central processor 210 regulates speeds of the arterial and venous pumps 104, 106 as desired to remove unwanted components from the whole blood 80 flowing into the filter 142. Filtered blood 90 flows from the venous pump 106, through the bubble detector 242, to the reinfusion bag 170, then returns to the patient. Optionally, a separate return pump (not shown) could be included to pump blood back to the patient. As in prior-art single-needle dialysis apparatus, filtered blood 90 accumulates before being returned to the patient, and a single inlet/outlet needle 274 allows for alternating removal and return of blood from and to the patient. The dialysis inlet bag 130 provides a source of whole blood 80 for proper operation of the arterial pump 104. As described for the two-needle dialysis apparatus 50, above, the inlet bag 130 can be eliminated if the patient can deliver blood quickly enough to meet the flow rate demands of the arterial pump 104. Since blood flows alternately through the same needle, however, some means of blood storage must be included in the single-needle dialysis apparatus 60. In some applications, the available volume of arterial and venous compliance chambers 182, 184 (as shown in the autotransfusion apparatus 40 depicted in FIG. 5) and/or the expansion capability of the flexible membrane fibers 148 of the filter 142 are sufficient to provide adequate blood storage during cycling of the single-needle dialysis apparatus 60.

Using the principles of the invention, the blood experiences a constant transmembrane pressure while passing through the filter 142, instead of the cyclical, inconstant pressurizing of conventional single-needle dialysis. The inefficiency arising from such oscillating transmembrane pressure is thus avoided. To achieve the same mean transmembrane pressure, as with prior art apparatus, lower interior pressure peaks are possible. The invention also thus reduces stresses and strains imposed on the apparatus and related equipment.

The present invention also provides an increased level of safety against flow of contaminating fluids, liquid or gas, into blood inside the filter 142 from the exterior chamber 154. Avoiding such reverse flow necessitates preventing a vacuum from occurring inside the filter 142. As a first level of safety, the central processor 210 monitors the signals from the arterial pressure sensor 220 and the venous pressure sensor 236. If the pressure at the filter outlet 146 were to exceed the pressure at the filter inlet 144, then a vacuum would exist inside the filter 142 relative to the exterior chamber 154. As a second level of safety, the central processor 210 also monitors the speeds of the arterial pump 104 and the venous pump 106. Again, if the pump rate of the venous pump 106 were to exceed the pump rate of the arterial pump 104, fluid in the exterior chamber 154 would be drawn into the interior of the fluid 142. The central processor monitors the various elements to ensure that an unwanted vacuum does not occur within the filter 142. The present invention thus provides two levels of safety, where the prior art apparatus affords only one, protecting the patient from blood contamination.

OXYGENATION APPARATUS

Figure 8:
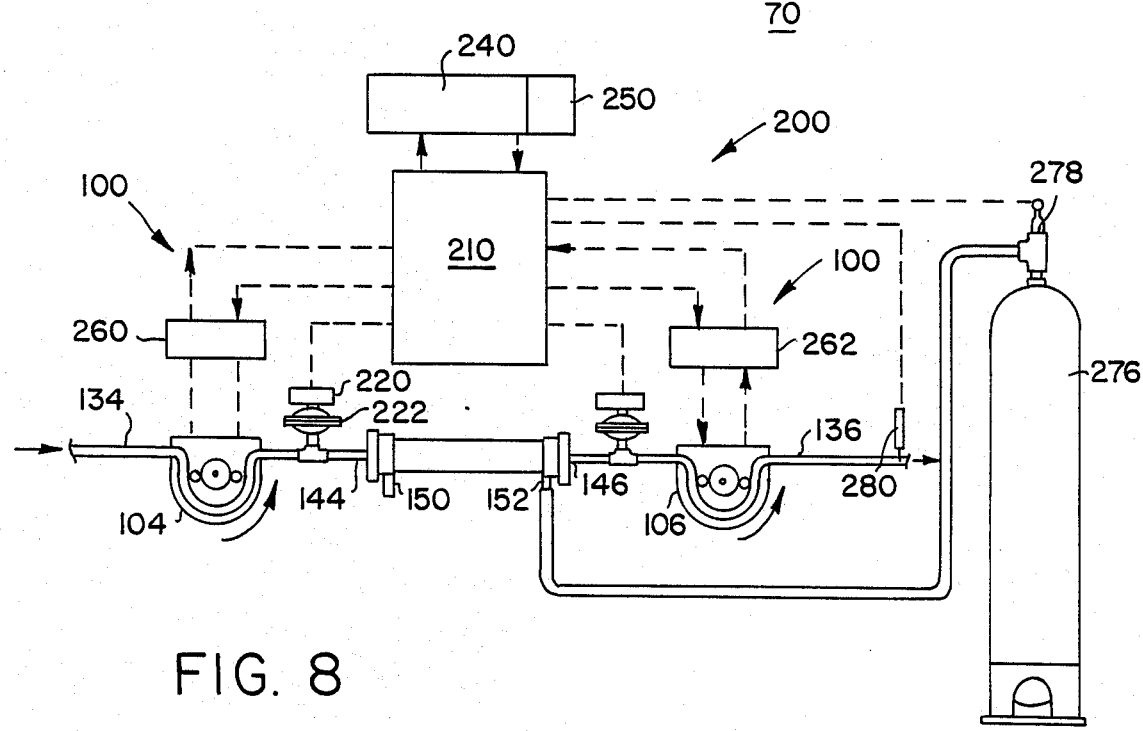
FIG. 8 illustrates a partial schematic diagram of a blood oxygenation apparatus employing principles of the invention.
Figure 9:
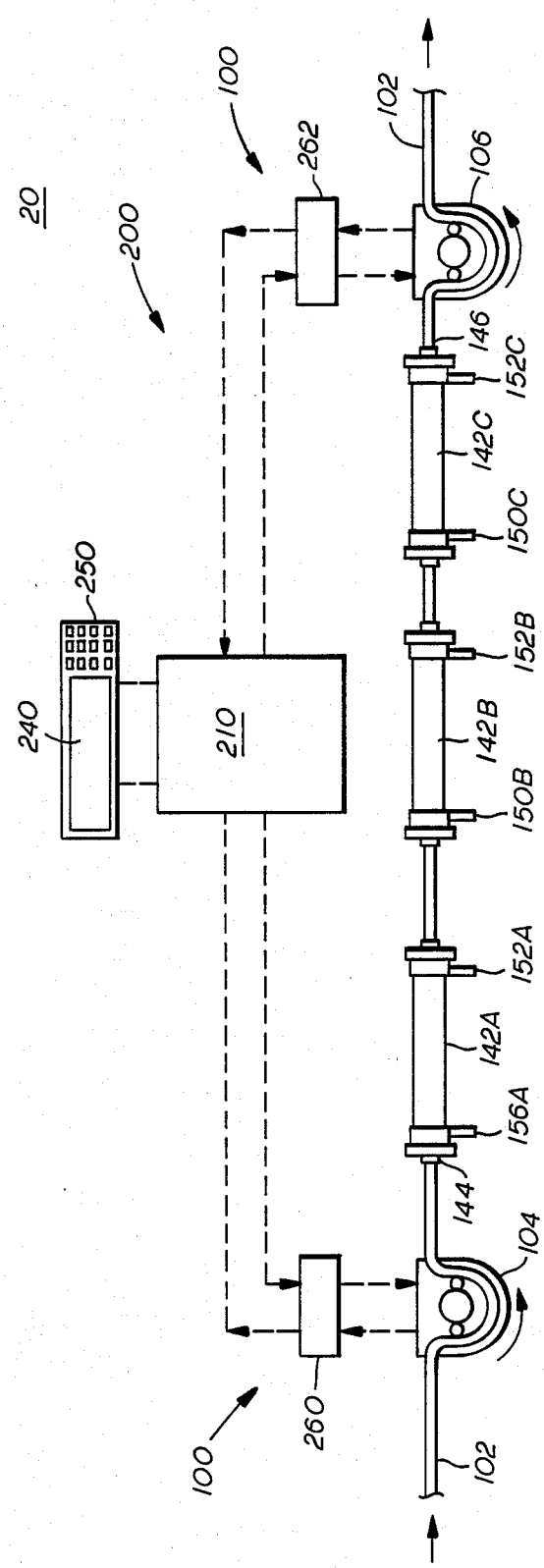
FIG. 9 is the extracorporeal circulation apparatus of FIG. 2, schematically depicting a series of filter means 142a, 142b, and 142c with each filter having varying filtration coefficients.

Referring now to FIG. 8, depicted therein is an oxygenation apparatus 70 constructed in accordance with the principles of the invention. Oxygen-poor blood flows into the oxygenation apparatus 70 through the inlet 134. Oxygen-enriched blood returns to the patient through the outlet 136. An oxygen source 276 connects to the chamber inlet 152; the chamber outlet 150 is open to the atmosphere. Oxygen from the oxygen source 276 flows into the exterior chamber 148. Carbon dioxide and unused oxygen exit via the chamber outlet 150. The central processor 210 is linked to an oxygen flow controller 278 at the outlet of the oxygen source 276. This oxygen flow controller 278 regulates the flow rate of oxygen from the oxygen source 276 in response to signals from the central processor 210. The central processor 210 monitors oxygen content of the treated blood downstream from the venous pump by means of a percent-oxygen indicator 280. The percent-oxygen indicator 280 is of a conventional type known to the prior art, using infrared absorption or other means to determine the percent of oxygen absorbed in the detected blood. A suitable percent-oxygen indicator 280 is the IBC Differential Oxygen Analyzer, Model 145-B, sold by Bentley, of California. The central processor 210 compares the oxygen percent detected with a predetermined, desired level of oxygen. If the blood oxygen content is too low, the central processor 210 can increase the oxygen flow through the oxygen flow controller 278. The central processor 210 can also adjust the arterial pump 104 speed as needed to maintain the desired transmembrane pressure based on known or measured oxygen pressure in the exterior chamber 154. This transmembrane pressure ensures that the flowing blood properly forms thin films along the membrane interior. The thin films of flowing blood provide maximum surface area for optimum oxygenation of the blood. By optimization of the pump rates and the oxygen flow rate, oxygen and carbon dioxide can most efficiently migrate across the membrane to be absorbed and discharged, respectively, by the red cells of the blood. The invention thus considerably enhances the efficiency and effectiveness of heart-lung machines by providing a precise and predictable means to control transmembrane pressure and flow rates while oxygenating blood.

Further modifications within the spirit of the invention include a combination of a plurality of treatment means 140 in series or parallel, with an associated circulating means 100 and control system 200. Connecting a plurality of treatment means in series would have, for example, fluid flowing from an inlet pump into a treatment means, from the outlet of the treatment means into the inlet of a second treatment means, the outlet of which second treatment means leads to an outlet pump. Between the two treatment means, there could be a pressure sensor, and an occluding device or a pump. The control system would regulate the occluding device or pump between the two treatment means, as well as the inlet pump and the outlet pump, to achieve desired operating parameters, such as calculated interior pressures within one or both treatment means.

Connecting a plurality of treatment means in parallel would, for example, have an outlet of an exterior chamber of a first treatment means connect to tubing leading to the inlet of a second treatment means. With this arrangement, the filtration effluent from the first treatment means would be filtered again through the second treatment means. Such repetitive filtration would prove very useful, as one example, in utilizing different types of treatment means having varying filtration coefficients and/or microporous membrane pore sizes. The first treatment means might yield, in its filtration effluent, particles too large to pass through the filter of the second treatment means. This arrangement thus would permit staged separation of blood into a number of components, as allowed by the number and nature of treatment means included.

Additionally, modification of the control system 200 to monitor and detect physical properties of the filtration effluent would be in accordance with the principles of the invention. Since various components of blood possess different characteristics, the control system 200 could adjust the circulating means 100 as necessary to obtain the desired component as a filtration effluent. The control system 200, instead of reading pressures, for example, could measure the optical or electrical characteristics of the filtraton effluent. Plasma, for instance, has unique optical characteristics apart from cellular components of the blood. If separation only of plasma were desired, the control system 200 could be equipped with an optical sensor monitoring the filtration effluent. Such a sensor could include a light source and a light detector. The light source would supply light of a wavelength that is absorbed only by the cellular components and not by the plasma. The light source might, for instance, have a white light and an appropriate light filter. Light of the selected wavelength would pass through the filtration effluent and be monitored by the light detector. When the cellular components are contained in the effluent, they would absorb the selected wavelength. The light detector would no longer receive the light, indicating non-plasma, cellular components had been detected. The optical sensor would then signal the control system 200. The control system 200, in turn, would adjust the flow rates of the circulating means 100, generally as described for the extracorporeal circulation apparatus 10, to maintain the desired filtration of plasma, free of such cellular components.

Such optical sensing and related control would find highly useful application, as one example, in an apparatus for staged component separation utilizing treatment means connected, as described above, in parallel. The optical sensors would detect the nature of fluids between various treatment means. The control system 200 then would adjust pumps and/or occluding devices upstream of, downstream of, and between, the various treatment means, as appropriate, to direct the blood components as desired among the treatment means.

While a preferred embodiment of the invention has been shown and described, further modifications thereof can be made by one skilled in the art without departing from the spirit of the invention.

What is claimed is:

1. Apparatus for filtering whole blood to selectively remove designated components thereof, comprising:
    a filter having a porous membrane for filtering the whole blood and passing the designated components through the pores of said porous membrane to remove the designated components as the whole blood passes through said filter at a predetermined filter rate;
    said filter having an exit at substantially atmospheric pressure for the disposal of the designated components;
    said filter having an inlet for the whole blood and an outlet for the filtrate resulting from the removal of the selected components, said filtrate having a varying volume substantially less than the volume of the whole blood as a result of the removal of the selected components from the whole blood by said filter;
    a first pump operating at a speed for pumping the whole blood to said inlet of said filter at a first flow rate;
    a second pump for pumping the filtrate of reduced volume from said outlet of said filter at a second flow rate;
    means for monitoring said first and second flow rates and independently adjusting said speed of each of said first and second pumps to maintain a constant differential between said first and second flow rates to thereby maintain said predetermined filter rate as the volume of the whole blood and reduced volume of the filtrate vary during filtration;
    fluid connecting means for providing a blood flow path from said first pump to said filter to said second pump; and
    said first and second pumps being peristaltic pumps fully occluding said fluid connecting means thereby acting as flowmeters to measure and regulate said first and second flow rates as the volumes vary during filtration.

2. Apparatus for filtering whole blood to selectively remove designated components thereof comprising:
    a filter for filtering the whole blood through a porous membrane to separate the designated components from the filtrate resulting from the filtration, the whole blood flowing interiorly of said filter on one side of said porous membrane at an interior pressure and the designated components flowing through said porous membrane to another side of said porous membrane at substantially atmospheric pressure to remove the designated components from the whole blood as the filtrate passes through said filter, the volume of said filtrate varying depending upon the amount of designated components removed and being substantially less than the volume of the whole blood;
    a first pump operating at a first speed for pumping the volume of whole blood through the interior on said one side of said filter at a first flow rate;
    a pressure monitoring means for sensing a first pressure of the whole blood between said first pump and said filter;
    a second pump operating at a second speed for regulating the flow rate of the reduced volume of the filtrate from the outlet of said filter;
    a second pressure monitoring means for sensing a second pressure of the reduced volume of the filtrate between said filter and said second pump;
    control means for reading said first and second pressures and speeds to determine said interior pressure and flow rates of the whole blood and filtrate and regulating said speeds of first and second pumps to maintain a predetermined interior pressure of said filter and flow rates of the whole blood and filtrate;
    fluid connecting means for providing a blood flow path from said first pump to said filter to said second pump; and
    said first and second pumps fully occluding said fluid connecting means to act as flowmeters to measure and regulate said flow rates as the volumes vary during filtration.

3. Apparatus for filtering whole blood to selectively remove designated components thereof and return the filtrate to the patient, comprising:
    a filter for filtering the whole blood through a porous membrane to remove the designated components from the whole blood and produce the resulting filtrate with the whole blood flowing interiorly of said filter on one side of said porous membrane at a predetermined interior pressure and the designated components flowing through said porous membrane to the other side of said porous membrane to remove the designated components as the whole blood passes through said filter, the volume of the filtrate varying depending upon the amount of designated components removed and being substantially less than the volume of the whole blood, said membrane having a given filter permeability;

a first peristaltic pump operating at a first speed for pumping the volume of whole blood through the interior of said filter at a first flow rate;

a pressure monitoring means for sensing the inlet pressure of the whole blood between said first pump and said filter;

a second peristaltic pump operating at a second speed for pumping the reduced volume of the filtrate from the outlet of said filter at a second flow rate to the patient's bloodstream having a higher pressure than the outlet pressure of said filter;

control means for reading said inlet pressure and said first flow rate to determine said interior pressure from said given filter permeability and regulating said speeds and flow rates of said first pump and said second pump to maintain said predetermined interior pressure;

fluid connecting means for providing a blood flow path from said first pump to said filter to said second pump; and said second pump having rollers fully occluding said fluid connectig means to force the filtrate into the patient's bloodstream against the higher pressure.

4. Apparatus for receiving whole blood from a patient, treating the whole blood, and returning the treated blood to the patient, comprising:

treatment means forming a first and second compartment having pores therebetween for treating the patient's whole blood to remove blood components therefrom by passing the damaged blood cells from said first compartment through said pores into said second compartment as the blood flows through said first compartment;

said second compartment having an exit to the ambient for the disposal of the damaged blood cells;

said first compartment having an inlet for the whole blood and an outlet for the treated blood, said treated blood having a reduced volume which varies according to the amount of blood components removed from the whole blood by said treatment means;

tubing means for receiving the patient's whole blood, circulating the whole blood to said inlet of said treatment means, and returning the treated blood from said outlet to the patient;

arterial pump means connected to said tubing means having a plurality of rollers fully occluding said tubing means to force the whole blood to flow to said inlet of said treatment means;

venous pump means connected to said tubing means and independent of said arterial pump means also having a plurality of rollers fully occluding said tubing means to force the treated blood from said treatment means back to the patient's bloodstream, the pressure of the treated blood downstream of said venous pump being greater than the pressure of the treated blood upstream of said venous pump; and control means for controlling said arterial pump means at a first rate and said venous pumpp at a second rate to regulate independently the treatment of the blood by said treatment means and the return of the treated blood to the patient.

5. The apparatus according to claim 4 wherein said treatment means includes at least one porous membrane for filtering the treated blood from the whole blood, and associated with said membrane is a sensor for monitoring said treated blood and signalling said control means to adjust the speed of said arterial pump and thus the whole blood flow rate to maintain a predetermined filtration rate of said treatment means.

6. An apparatus for receiving whole blood from a patient, filtering the whole blood to selectively remove designated components thereof, and returning the filtrate to the patient comprising:

receiver means for receiving the patient's whole blood;

filter means having a porous membrane dividing said filter means into first and second chambers for filtering the whole blood and selectively passing the designated components from said first chamber through the pores of said porous membrane into said second chamber to remove the designated components as the whole blood passes through said first chamber of said filter means at a predetermined pressure;

said second chamber having an exit to the ambient for the disposal of the designated components;

said first chamber having an inlet for the whole blood and an outlet for the filtrate, said filtrate having a reduced volume which varies according to the amount of designated components removed from the whole blood;

return means for returning the filtrate to the patient;

tubing for circulating the blood among said receiver means, filter means and return means;

an arterial pump connected to said tubing and having a plurality of rollers fully occluding said tubing and operating at a first speed for pumping the blood from said receiver means to said inlet of said filter means at a first flow rate;

first pressure monitoring means for monitoring the inlet pressure of the whole blood between said arterial pump and the inlet of said filter means;

a venous pump connected to said tubing and having a plurality of rollers fully occluding said tubing and independently operating at a second speed for pumping the filtrate of reduced volume from the outlet of said filter means to said return means to the patient's bloodstream having a higher pressure than the outlet pressure of said filter at a second flow rate;

second pressure monitoring means for monitoring the outlet pressure of the reduced volume of the filtrate between said venous pump and the outlet of said filter means;

said venous pump being a positive displacement pump which displaces a predetermined volume of filtrate independent of the pressure of the whole blood, said pumps acting as flowmeters to regulate said flow rates as the volumes vary during filtration; and control means for reading said inlet and outlet pressures of said first and second pressure monitoring means and said speeds of said pumps for regulating said first and second flow rates to maintain said predetermined pressure of said filter means.

7. The apparatus according to claim 6 wherein said receiver means includes a cardiotomy and an accumulator for accumlating the blood prior to the blood being pumped to said cardiotomy.

8. The apparatus according to claim 7 wherein said cardiotomy is disposed upstream of said filter means for collecting the whole blood and allowing release of air entrained in such whole blood.

9. The apparatus according to claim 8 wherein said cardiotomy has within it a gross contaminant filter for filtering whole blood.

10. The apparatus according to claim 9 wherein said cardiotomy has associated therewith a level detector for detecting the level of whole blood within said cardiotomy.

11. The apparatus according to claim 8 wherein said cardiotomy has associated therewith a vent for release of air.

12. The apparatus according to claim 6 wherein said receiver means has a needle bearing outwardly therefrom for receiving whole blood from the patient's circulatory system.

13. The apparatus according to claim 6 wherein said receiver means includes a suction wand for gathering the patient's whole blood from a location outside the patient's blood vessels, said suction wand being attached to said tubing upstream of said receiver means.

14. The apparatus according to claim 13 wherein attached to said suction wand is an anticoagulant tube for adding anticoagulant to whole blood collected by said suction wand.

15. The apparatus according to claim 14 wherein a collection pump is located in the blood flow path for providing suction for said suction wand.

16. The apparatus according to claim 14 wherein said cardiotomy has on its outer surface a vacuum port for connecting to a vacuum source and thereby to provide suction for said suction wand.

17. The apparatus according to claim 6 wherein said filter means includes a filter having a microporous membrane surrounded by a chamber.

18. The apparatus according to claim 17 wherein said microporous membrane is shaped into a hollow fiber.

19. The apparatus according to claim 17 wherein said microporous membrane is shaped into a flat plate.

20. The apparatus according to claim 17 wherein said microporous membrane is shaped into a coil.

21. The apparatus according to claim 17 wherein the whole blood passes through said microporous membrane at said predetermined pressure.

22. The apparatus according to claim 21 wherein said chamber maintains an external pressure exterior to said microporous membrane which is less than said predetermined pressure, the differential between said external pressure and said predetermined pressure being the transmembrane pressure, whereby as the whole blood passes through said membrane, the designated components in the whole blood to be selectively removed pass through the walls of said microporous membrane due to said transmembrane pressure, thereby removing the designated components from the whole blood and permitting the filtrate to pass from said filter means for return to the patient.

23. The apparatus according to claim 22 wherein said external pressure is substantially atmospheric pressure.

24. The apparatus according to claim 22 wherein said chamber includes inlet and outlet ports for attachment to pressure means for maintaining a predetermined external pressure in said chamber and thus a predetermined transmembrane pressure.

25. The apparatus according to claim 24 wherein the designated components exits said chamber via said outlet port.

26. The apparatus according to claim 21 wherein there is maintained within said chamber an external pressure exterior to said microporous membrane which is greater than said predetermined pressure, said chamber having preselected fluids which pass through said microporous membrane for absorption by the blood.

27. The apparatus according to claim 6 further including an oxygenator providing for oxygenation of the patient's blood.

28. The apparatus of claim 7 wherein said filter means includes a plurality of filters connected in series, said filters having varying filtration coefficients permitting a staged separation of the designated components from the whole blood.

29. The apparatus according to claim 6 wherein said arterial pump is a roller pump having rollers that spin and push against said tubing, causing blood to flow through said tubing.

30. The apparatus according to claim 6 and further comprising replaceable isolators for isolating said first and second monitoring means from blood within said tubing.

31. The apparatus according to claim 6 wherein said filter means includes a processing device having operating characteristics varying in accordance with said inlet and outlet pressures.

32. The apparatus according to claim 6 wherein said tubing further circulates the blood to a chamber means for receiving the blood to homogenize the pressure of the blood.

33. The apparatus according to claim 6 wherein said control means includes:
pump controllers for regulating the speed of said arterial and venous pumps; and
a central processor for reading said inlet and outlet pressures from said first and second pressure monitoring means, determining any deviation from said predetermined pressure in said filter means, and signalling said pump controllers to adjust said speed of said arterial pump to correct any said deviation to maintain said predetermined pressure.

34. The apparatus according to claim 33 wherein said arterial and venous pumps are independently regulated by said control means.

35. The apparatus according to claim 33 wherein said control means maintains said predetermined pressure by regulating said speed of said arterial pump via one of said pump controllers.

36. The apparatus according to claim 33 wherein said first and second pressure monitoring means continually transmit pressure readings to said central processor.

37. The apparatus according to claim 33 and further comprising an input device connected to said central processor for input of predetermined operational parameters.

38. The apparatus according to claim 37 and further comprising a display device for displaying operational parameters.

39. The apparatus according to claim 38 wherein said input device is an electronic keypad.

40. The apparatus according to claim 39 wherein said display device is an alphanumeric display.

41. The apparatus according to claim 33 further including a return means for returning the filtrate to the patient and a pressure sensor for opening and outlet of said return means and closing an inlet to said return means when pressure of the filtrate downstream of said venous pump reaches a predetermined limit.

42. The apparatus according to claim 33 wherein said tubing further circulates the blood to a bubble detector for sensing bubbles in blood and relaying a signal to said control means upon sensing such bubbles.

43. The apparatus according to claim 42 wherein:
said bubble detector relays said signal to said central processor upon sensing such bubbles; and
said control means causes said arterial and venous pumps to cease pumping upon receiving said signal from said bubble detector.

44. The apparatus according to claim 43 wherein:
said bubble detector allows said arterial and venous pumps to pump fluid through said tubing before such fluid initially flows past said bubble detector; and
said bubble detector is armed after sensing such fluid, thereafter relaying said signal to said control means upon sensing such bubbles.

45. The apparatus according to claim 6 and wherein said tubing further circulates the blood to a storage means for storing the treated blood.

46. The apparatus accordign to claim 45 wherein said storage means includes a level sensor for detecting the level of blood in said storage means.

47. The apparatus according to claim 45 wherein said tubing further circulates the blood to means for alternately opening and closing an inlet to and an outlet from said storage means.

48. The apparatus according to claim 6 wherein downstream of said filter means said tubing circulates the filtrate to an outlet fileter for filtering the filtrate before returning the filtrate to the patient.

49. The apparatus according to claim 41 wherein said return means includes a needle extending from said return means for returning the filtrate to the patient's circulatory system.

50. An apparatus for receiving a patient's whole blood, filtering the whole blood to selectively remove designated components thereof, and returning the filtered blood to the patient, comprising:
an accumulator for accumulating the patient's whole blood;
receiver means for receiving the patient's whole blood from said accumulator, including a cardiotomy for collecting the patient's whole blood and releasing air from the whole blood;
filter means for filtering the whole blood through a porous membrane to separate the designated components from the filtrate as the whole blood passes through said filter means at a predetermined pressure to remove the designated components by flowing the designated components through said membrane to the other side of said membrane at atmospheric pressure;
return means for returning the filtered blood to the patient, the filtered blood having a reduced volume which varies according to the amount of designated components removed from the whole blood;
an arterial pump operating at a speed for pumping the whole blood from said receiver means to said filter means;
first pressure monitoring means for continually monitoring inlet pressure of the whole blood between said arterial pump and the inlet of said filter means;
a venous pump for pumping the filtered blood from said filter means to said return means at a constant flow rate;
second pressure monitoring means for continually monitoring the outlet pressure of the filtered blood between said venous pump and the outlet of said filter means;
tubing means for circulating the blood among said receiver means, treatment means, arterial and venous pumps, and return means;
said pumps having a plurality of rollers fully occluding said tubing means to act as flowmeters to measure and regulate said flow rates as the volumes vary during filtration, said venous pump forcing the filtered blood downstream into the patient's bloodstream at a pressure higher than the outlet pressure;
control means, having pump controllers for independently regulating the speed of said arterial and venous pumps, and having a central processor for reading said inlet and outlet pressures of said first and second pressure monitoring means and regulating said speed of said arterial pump to maintain said predetermined pressure of said filter means;
said control means including an input device connected to said central processor for input of predetermined operational parameters; and
a display device connected to said central processor for displaying operational parameters.

51. A method of filtering whole blood to selectively remove designated components thereof, comprising the steps of:
removing whole blood from a patient utilizing tubing extending to a filter;
pumping blood through the tubing using a pump having a plurality of rollers which fully occlude the tubing as the rollers rotate at a first speed;
passing the whole blood into a first chamber of the filter;
filtering the designated components through a porous membrane at a predetermined pressure into a second chamber at atmospheric pressure;
passing the filtrate having a reduced volume from the filter into a tubing extending to the patient;
pumping the filtrate through the tubing utilizing a second pump having a plurality of rollers which fully occlude the tubing at a second flow rate;
sensing said filter pressure and said second flow rate;
regulating said first flow and said second flow rates to maintain a predetermined filter pressure; and
pumping the filtrate into the patient's bloodstream at a pressure higher than the outlet pressure of the filter.

52. A method of filtering whole blood to selectively remove designated components thereof according to claim 56 further comprising:
releasing entrained air from the blood;
oxygenating the blood;
controlling the first and second flow rates to independently filter the whole blood at said specified rate and control the rate at which filtered blood is pumped back to the patient.

53. The method of claim 52 further including:
sensing bubbles in the blood; and
ceasing pumping of blood upon sensing of said bubbles.

54. The method of claim 52 further including:
withdrawing whole blood from the patient by suction; and adding anticoagulant to the withdrawn whole blood.

* * * * *